United States Patent [19]

Oonishi et al.

[11] Patent Number: 4,694,102

[45] Date of Patent: Sep. 15, 1987

[54] CALCIUM CARBOXYLATE PHENOL DERIVATIVE

[75] Inventors: Akiyoshi Oonishi; Kenji Tanaka, both of Yokkaichi; Makoto Tadeka, Ami; Kazuhiko Konno, Ami; Masaki Saito, Ami, all of Japan

[73] Assignee: Mitsubishi Yuka Fine Chemicals Co., Ltd., Tokyo, Japan

[21] Appl. No.: 866,280

[22] Filed: May 23, 1986

Related U.S. Application Data

[62] Division of Ser. No. 584,636, Feb. 29, 1984, Pat. No. 4,633,008.

[30] Foreign Application Priority Data

Mar. 15, 1983 [JP] Japan .................................. 58-42694
Jul. 6, 1983 [JP] Japan .................................. 58-122568

[51] Int. Cl.$^4$ ............................................ C07C 149/20
[52] U.S. Cl. .................................................... 562/426
[58] Field of Search ........................................ 562/426

[56] References Cited

U.S. PATENT DOCUMENTS 4,571,430 2/1986 Byrne et al. ........................ 562/426

Primary Examiner—Henry R. Jiles
Assistant Examiner—J. G. Mullins
Attorney, Agent, or Firm—Oblon, Fisher, Spivak, McClelland, Maier

[57] ABSTRACT

A phenol derivative represented by the formula

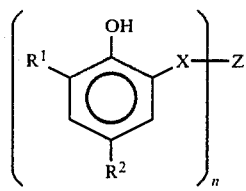

wherein $R^1$ is a secondary or tertiary hydrocarbon residue of having 3 to 8 carbon atoms, $R^2$ is a hydrocarbon residue having 1 to 12 carbon atoms, X is

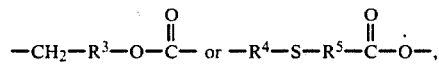

wherein $R^3$, $R^4$ and $R^5$ each is an alkylene group having 1 to 4 carbon atoms, Z is an n-valent group and n is an integer of 1 to 8.

This compound is effective to prevent the oxidation of organic materials.

1 Claim, No Drawings

CALCIUM CARBOXYLATE PHENOL DERIVATIVE

This is a division of application Ser. No. 584,636, filed Feb. 29, 1984, now U.S. Pat. No. 4,633,008.

FIELD OF THE INVENTION

The present invention relates to a novel phenol derivative. The compound of this invention is effective to prevent the oxidation of various organic materials.

BACKGROUND OF THE INVENTION

Organic materials such as natural polymers, synthetic polymers, oils and fats, lubricating oils or hydraulic fluids, lose their usefulness when oxidized. Therefore, various antioxidants have been devised to add to such organic materials. For example, it is known that hindered phenols, organic sulfur compounds, organic phosphorus compounds, and aromatic amines are effective antioxidants, which are used alone or in combination with each other. Examples of derivatives having the hindered phenol skeleton are disclosed in Japanese Patent Publication Nos. 2488/1958, 17164/1963, and 9651/1967. Those compounds are now practically used. Unexamined Published Japanese Patent Application Nos. 59835/1972, 128656/1982, and 128679/1982 disclose hindered phenol derivatives as the antioxidants. These conventional antioxidant compounds are not necessarily satisfactory under very severe conditions.

SUMMARY OF THE INVENTION

Accordingly, an object of this invention is to provide a specific phenol derivative to overcome the disadvantages in the conventional compounds.

The phenol derivative is the compound represented by formula (I)

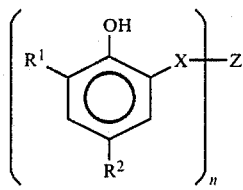

wherein $R^1$ is a secondary or tertiary hydrocarbon residue having 3 to 8 carbon atoms, $R^2$ is a hydrocarbon residue having 1 to 12 carbon atoms, X is

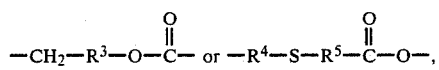

wherein $R^3$, $R^4$, and $R^5$ each is an alkylene group having 1 to 4 carbon atoms, Z is an n-valent group, and n is an integer of 1 to 8.

The compound of formula (I) is effective to prevent the oxidation of organic materials. The compound is also effective to prevent the oxidation of synthetic high molecular weight materials such as polyolefin (e.g., polyethylene, polypropylene or ethylene-propylene copolymer); polystyrene; polyvinyl chloride; and ABS resin, which are exposed under severe oxidizing conditions when they are molded and are used as the final products.

DETAILED DESCRIPTION OF THE INVENTION

The phenol derivative of this invention is represented by the formula (I) described above.

The group X is limited to bond to the specific position (i.e., o-position) of the phenol nucleus, and is

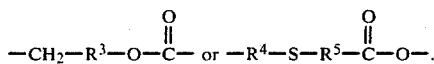

Therefore, the formula (I) is, for the simplicity, represented by the formula (II)

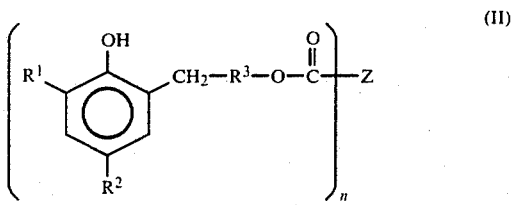

wherein $R^1$ is a secondary or tertiary hydrocarbon residue having 3 to 8 carbon atoms, $R^2$ is an alkyl group having 1 to 12 carbon atoms, $R^3$ is an alkylene group having 1 to 4 carbon atoms, Z is an n-valent organic group, and n is an integer of 1 to 8 or the formula (III)

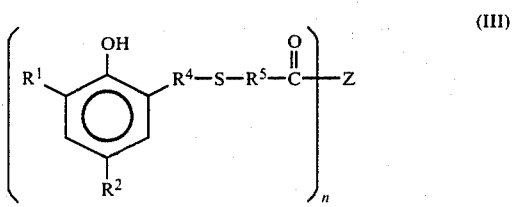

wherein $R^1$ is a secondary or tertiary hydrocarbon residue having 3 to 8 carbon atoms, $R^2$ is a hydrocarbon residue having 1 to 12 carbon atoms, $R^4$ and $R^5$ each is an alkylene group having 1 to 4 carbon atoms, Z is an n-valent group, and n is an integer of 1 to 8.

Phenol Derivatives Represented By Formula (II)

In the formula (II), $R^1$ is a secondary or tertiary hydrocarbon residue having 3 to 8 carbon atoms.

Examples of the hydrocarbon residues include isopropyl, isobutyl, tertiary butyl, secondary and tertiary pentyl, hexyl, heptyl, and octyl, which are of chain structure, and also include 1-methylcyclohexyl, 1-phenylethyl, and norbornyl, which are of cyclic structure. Of these, the most preferred examples are tertiary butyl and 1-methylcyclohexyl.

$R^2$ is an alkyl group having 1 to 12 carbon atoms.

Example of the alkyl group include methyl, ethyl, propyl, butyl, pentyl, hexyl, heptyl, octyl, nonyl, decyl, undecyl, and dodecyl, which are of chain structure, and also include 1-methylcyclohexyl, 1-phenylethyl, and norbornyl, which are of cyclic structure. Of these, preferred examples as antioxidants are methyl and tertiary butyl.

$R^3$ is an alkylene group having 1 to 4 carbon atoms.

Examples of the alkylene group include methylene, ethylene, trimethylene, propylene, tetramethylene, and ethylethylene (These examples are applied to another alkylenes described below). Of these, the preferred example is ethylene.

Z is an n-valent organic group.

One group of Z is a hydrocarbon residue. Examples thereof include $C_1-C_{17}$ alkyl, $C_1-C_{10}$ alkylene, $C_3-C_{10}$ 3 to 8-valent aliphatic hydrocarbon residue (e.g., 1,2,3-propanetriyl), phenyl, 1,3,5-benzenetriyl, and 1,2,4,5-benzenetetrayl.

Another group of Z is a group containing sulfur atom(s). Examples thereof include $-R^a-S-R^b-$ (wherein $R^a$ and $R^b$ each is a $C_1-C_{10}$ alkylene, preferably $R^a$ and $R^b$ each is $-CH_2CH_2-$); $R^c+S-R^d\}_p$ (wherein $R^c$ is a p-valent hydrocarbon residue (e.g., 2 (or 3), 5 (or 6)-bicyclo[2.2.1]heptanediyl, 3 (or 4 or 5), 8 (or 9)-tricyclo[5.2.1.0$^{2,6}$]decanediyl, or cyclododecanetriyl, and $R^d$ is each a $C_1-C_{10}$ alkylene (preferably $-CH_2CH_2-$)); and

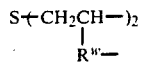

(wherein $R^w$ is a $C_1-C_{10}$ alkylene).

Further group of Z is a group containing nitrogen atom(s). Examples thereof include $N+R^e\}_3$ (wherein $R^e$ each is a $C_1-C_{10}$ alkylene, preferably $R^e$ is all $-CH_2-$).

Still another group of Z is a group containing oxygen atom(s). Examples thereof include $-R^f-O-R^g-$ (wherein $R^f$ and $R^g$ each is a $C_1-C_{10}$ alkylene, preferably $+CH_2-$), $C+R^h-O-R^i\}_4$ (wherein $R^h$ and $R^i$ each is a $C_1-C_{10}$ alkylene, preferably $R^h$ each is $-CH_2-$ and $R^i$ each is $-CH_2CH_2-$), and

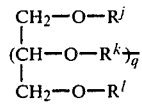

(wherein $R^j$, $R^k$, and $R^l$ each is a $C_1-C_{10}$ alkylene, preferably $-CH_2-$, and q is an integer of 0 to 5).

Still further group of Z is a group containing at least two of sulfur atom, nitrogen atom, and oxygen atom. Examples thereof include

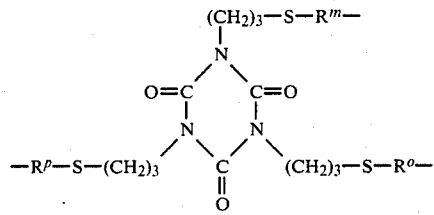

(wherein $R^m$, $R^o$, and $R^p$ each is a $C_1-C_{10}$ alkylene),

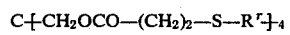

(wherein $R^r$ is a $C_1-C_{10}$ alkylene),

(wherein $R^s$ is a $C_1-C_{10}$ alkylene),

(wherein $R^t$ is a $C_1-C_{10}$ alkylene), and

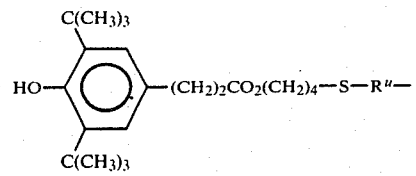

(wherein $R^u$ is a $C_1-C_{10}$ alkylene).

The oxygen-containing Z includes a group formed by esterifying the 8 hydroxyl groups in sucrose with $-R^v-S-CH_2CH_2COO-$ (wherein $R^v$ is a $C_1-C_{10}$ alkylene).

Of these, the most preferred group is a group represented by the formula

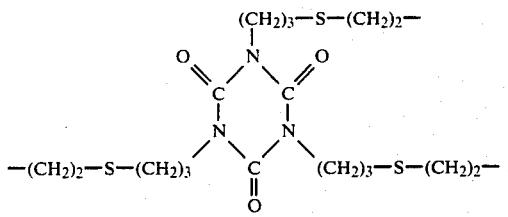

Representative examples of the phenol derivative represented by the formula (II) are shown below. The numbers designating the compounds will be referred to in the Examples and Application Examples described after.

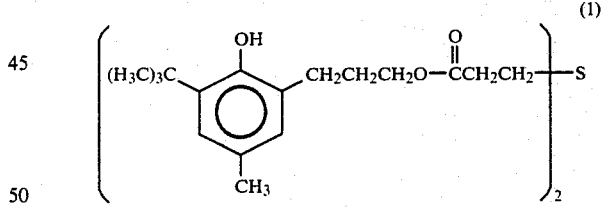

Bis[3-(3-tert-butyl-2-hydroxy-5-methylphenyl)-propyl]3,3'-thiodipropionate

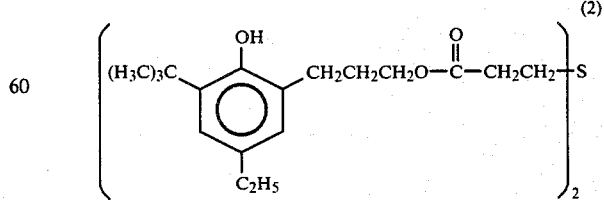

Bis[3-(3-tert-butyl-5-ethyl-2-hydroxyphenyl)-propyl]3,3'-thiodipropionate

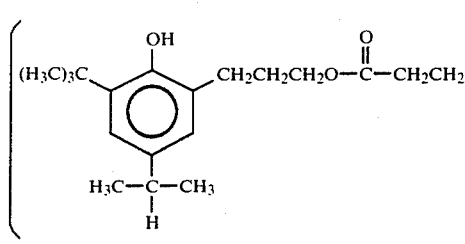

Bis[3-(3-tert-butyl-2-hydroxy-5-isopropylphenyl)-propyl]3,3'-thiodipropionate

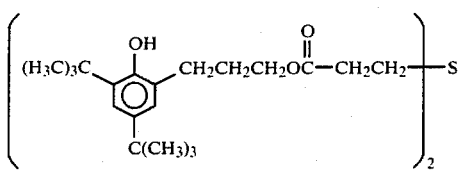

Bis[3-(3,5-di-tert-butyl-2-hydroxyphenyl)propyl]3,3'-thiodipropionate

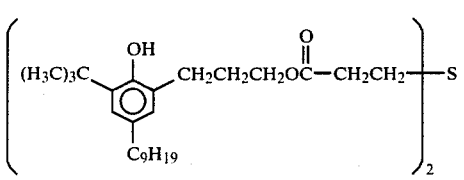

Bis[3-(3-tert-butyl-2-hydroxy-5-nonylphenyl)-propyl]3,3'-thiodipropionate

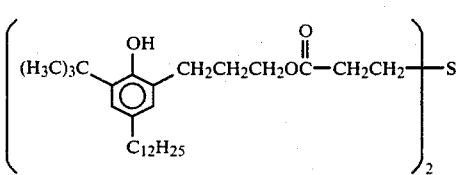

Bis[3-(3-tert-butyl-2-hydroxy-5-dodecylphenyl)-propyl]3,3'-thiodipropionate

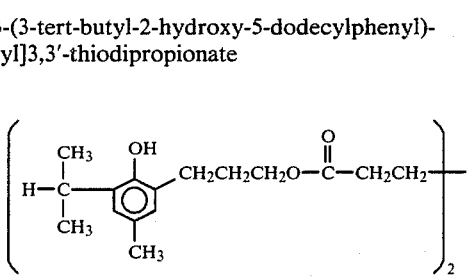

Bis[3-(2-hydroxy-3-isopropyl-5-methylphenyl)-propyl]3,3'-thiodipropionate

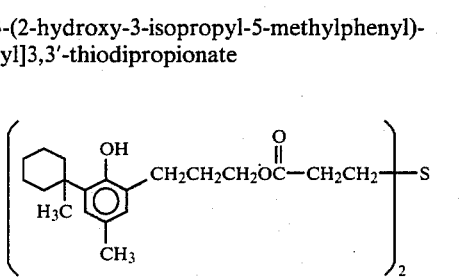

Bis[3-[2-hydroxy-3-(1-methylcyclohexyl)-5-methylphenyl)]propyl]3,3'-thiodipropionate

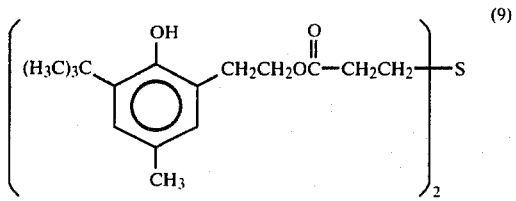

Bis[2-(3-tert-butyl-2-hydroxy-5-methylphenyl)ethyl]3,3'-thiodipropionate

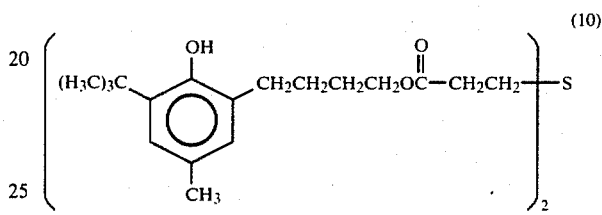

Bis[4-(3-tert-butyl-2-hydroxy-5-methylphenyl)-butyl]3,3'-thiodipropionate

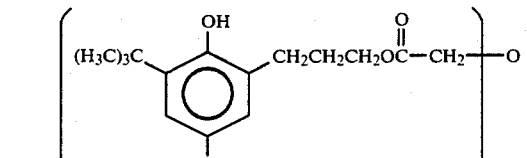

Bis[3-(3-tert-butyl-2-hydroxy-5-methylphenyl)propyl]-heptanedioate

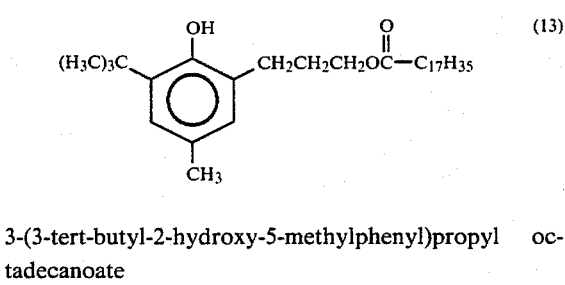

Bis[3-(3-tert-butyl-2-hydroxy-5-methylphenyl)propoxycarbonylmethyl]ether 3-(3-tert-butyl-2-hydroxy-5-methylphenyl)propyl octadecanoate

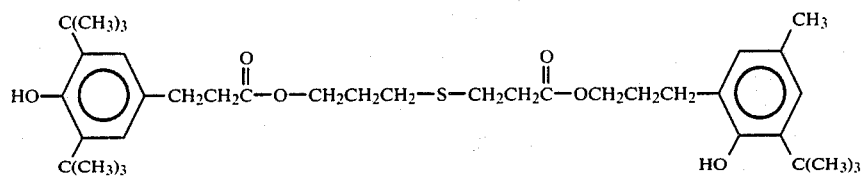

3-(3-tert-butyl-2-hydroxy-5-methylphenyl)propyl 3-[3-[2-(3,5-di-tert-butyl-4-hydroxyphenyl)ethylcarbonyloxy]propylthio]propionate

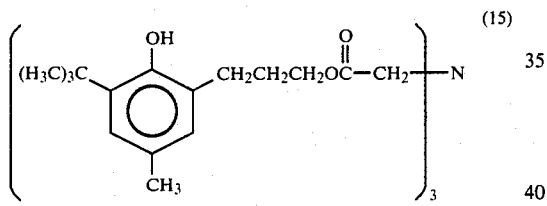

Tris[3-(3-tert-butyl-2-hydroxy-5-methylphenyl)propoxycarbonylmethyl]amine

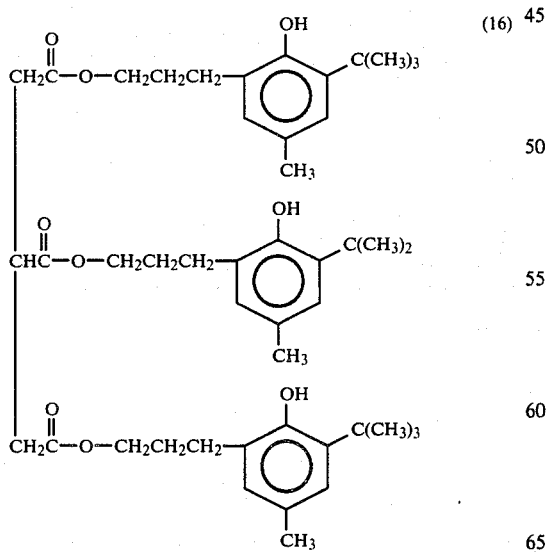

Tris[3-(3-tert-butyl-2-hydroxy-5-methylphenyl)-propyl]1,2,3-propanetricarboxylate

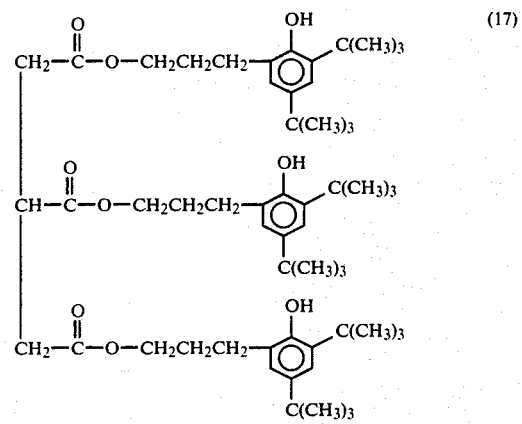

Tris[3-(3,5-di-tert-butyl-2-hydroxyphenyl)propyl]1,2,3-propanetricarboxylate

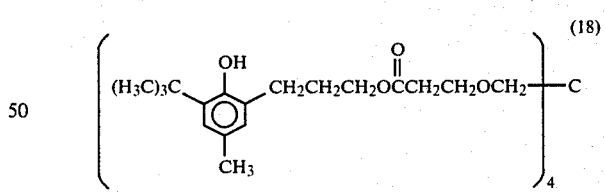

Tetrakis[2-[3-(3-tert-butyl-2-hydroxy-5-methylphenyl)-propoxycarbonyl]ethyloxymethyl]methane

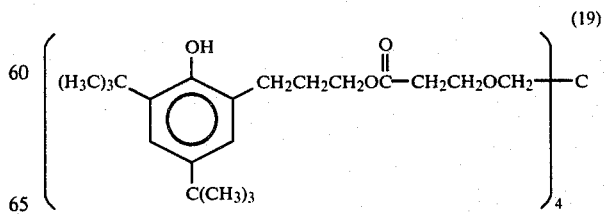

Tetrakis[2-[3-(3,5-di-tert-butyl-2-hydroxyphenyl)-propoxycarbonyl]ethyloxymethyl]methane

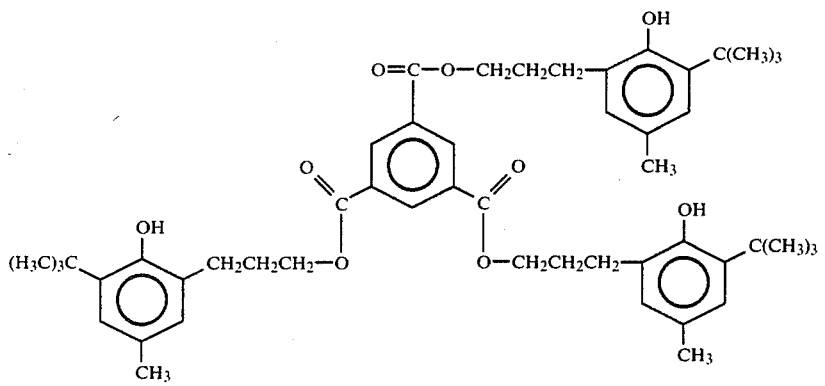
1,3,5-tris[3-(3-tert-butyl-2-hydroxy-5-methylphenyl)-propoxycarbonyl]benzene
1,3,5-tris[3-[2-[3-(3-tert-butyl-2-hydroxy-5-methylphenyl)propoxycarbonyl]ethylthio]propyl]-1,3,5-triazine-2,4,6(1H,3H,5H)-trione
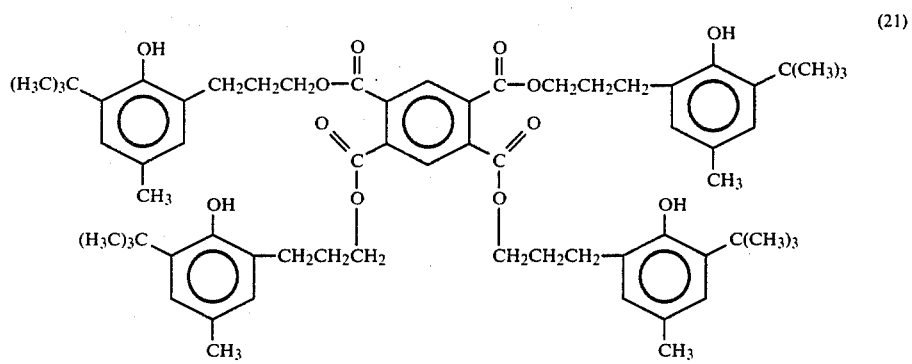
1,2,4,5-tetrakis[3-(3-tert-butyl-2-hydroxy-5-methylphenyl)propoxycarbonyl]benzene
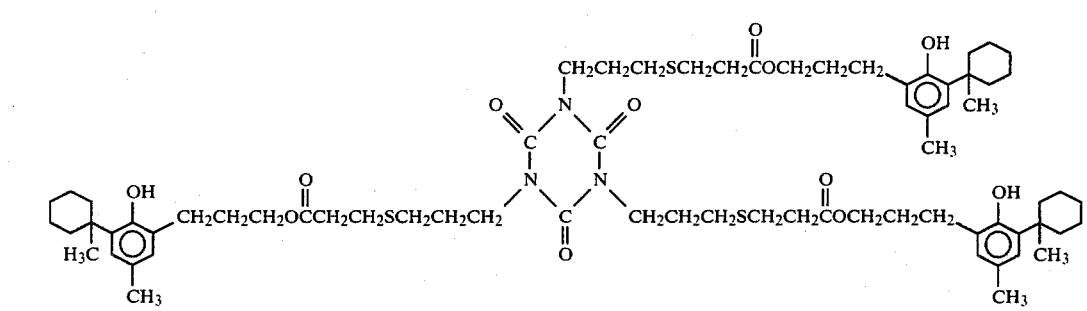
1,3,5-tris[3-[2-[3-[2-hydroxy-3-(1-methylcyclohexyl)-5-methylphenyl]propyloxycarbonyl]ethylthio]propyl]-1,3,5-triazine-2,4,6(1H,3H,5H)-trione
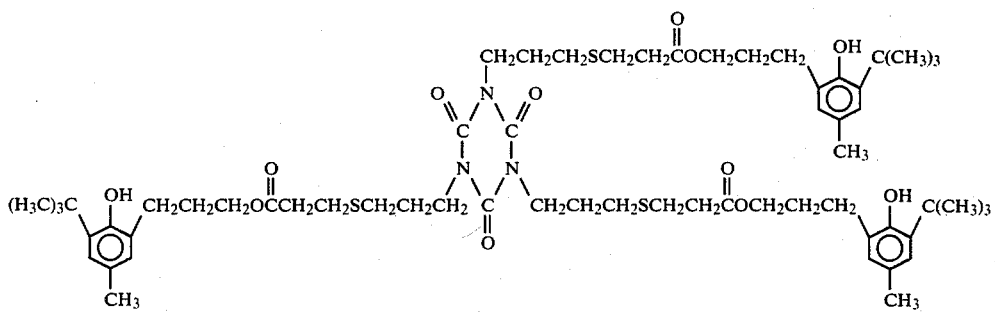

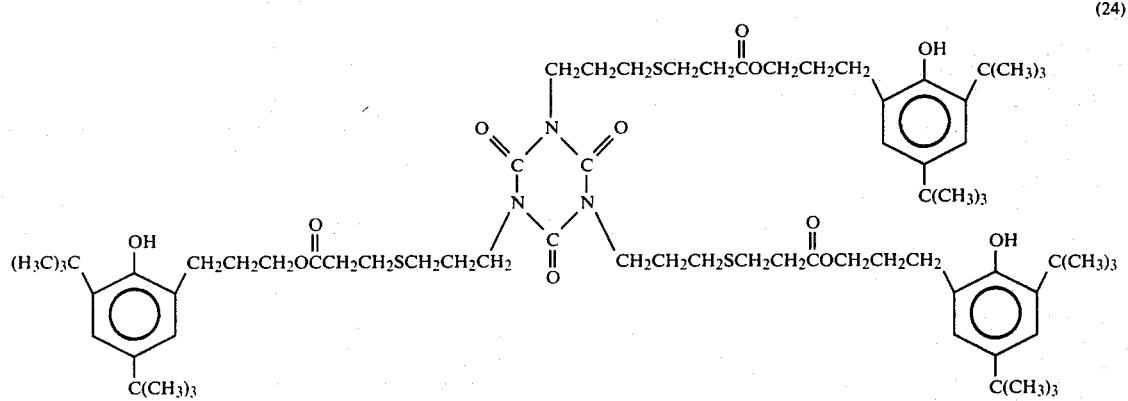

1,3,5-tris[3-[2-[3-(3,5-di-tert-butyl-2-hydroxyphenyl)-propoxycarbonyl]ethylthio]propyl]-1,3,5-triazine-2,4,6(1H,3H,5H)-trione

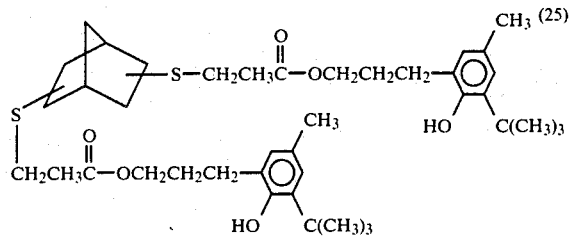

2(or 3),5(or 6)-bis[2-[3-(3-tert-butyl-2-hydroxy-5-methylphenyl)propoxycarbonyl]ethylthio]bicyclo[2.2.1]heptane

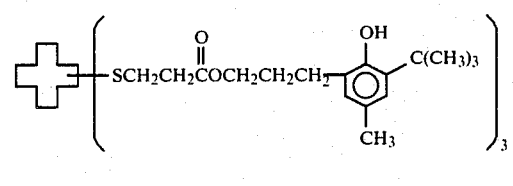

Tris[2-[3-(3-tert-butyl-2-hydroxy-5-methylphenyl)-propoxycarbonyl]ethylthio]cyclododecane

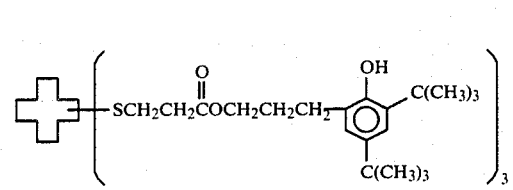

Tris[2-[3-(3,5-di-tert-butyl-2-hydroxyphenyl)propoxycarbonyl]ethylthio]cyclododecane

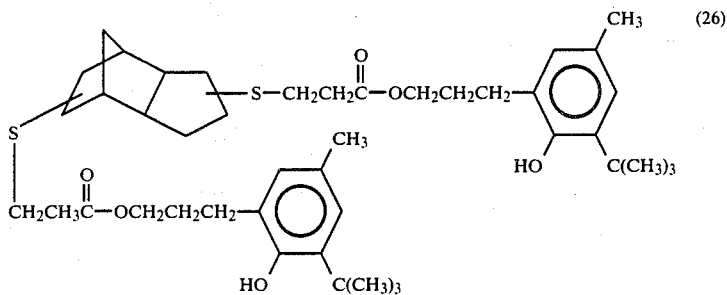

3(or 4 or 5),8(or 9)-bis[2-[3-(3-tert-butyl-2-hydroxy-5-methylphenyl)propoxycarbonyl]ethylthio]tricyclo[5.2.1.0^{2,6}]decane

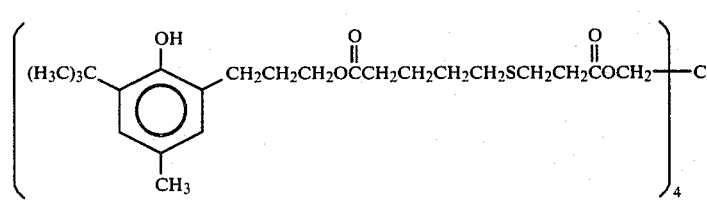

Tetrakis[3-[4-[3-(3-tert-butyl-2-hydroxy-5-methylphenyl)propoxycarbonyl]butylthio]propionyloxymethyl]methane

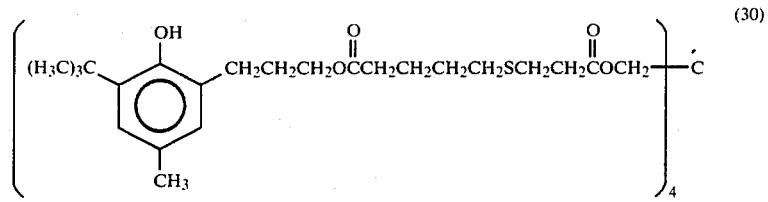

Tetrakis[3-[4-[3-(3,5-di-tert-butyl-2-hydroxyphenyl)-propoxycarbonyl]butylthio]propionyloxymethyl]methane

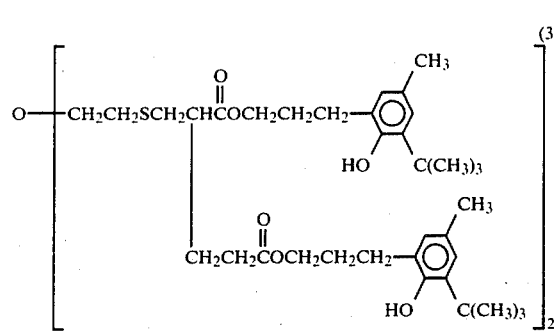

Bis[2-[2,4-bis[3-(3-tert-butyl-2-hydroxy-5-methylphenyl)propoxycarbonyl]butylthio]ethyl]ether

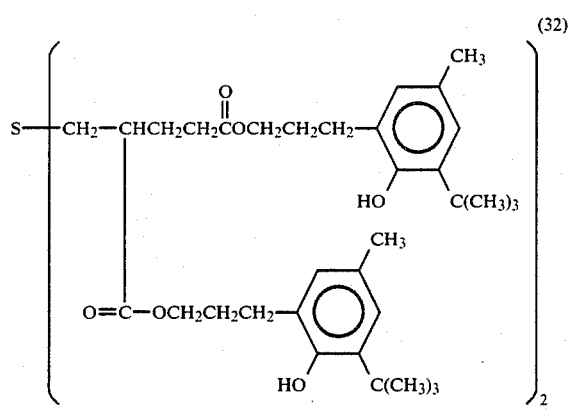

Bis[2,4-bis[3-(3-tert-butyl-2-hydroxy-5-methylphenyl)propoxycarbonyl]butyl]sulfide

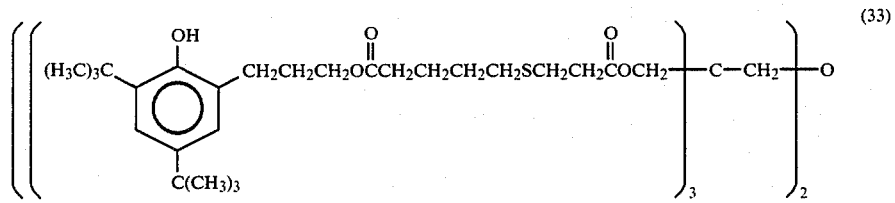

Hexakisester of dipentaerythritol and 3-[4-[3-(3,5-di-tert-butyl-2-hydroxyphenyl)propoxycarbonyl]butylthio]propionic acid

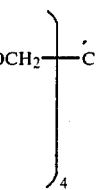

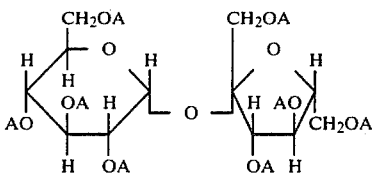

Octakisester of sucrose and 3-[4-[3-(3,5-di-tert-butyl-2-hydroxyphenyl)propoxycarbonyl]butylthio]propionic acid

Synthesis of Compound (II)

The compound (II) of this invention can be synthesized in any manner by introducing or forming specific groups or linkages.

The representative example of the synthesis is the reaction of an alcohol of the formula (IV) shown below with a carboxylic acid of the formula (V) shown below under the ester formation conditions.

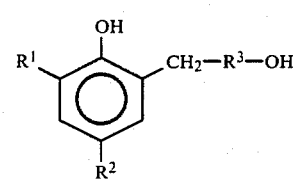

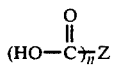

wherein $R^1$, $R^2$, $R^3$, Z, and n each is the same as defined in the formula (II) above.

"Reaction under the ester formation condition" means that the two compounds are reacted directly, preferably in the presence of an esterification catalyst; the carboxylic acid is reacted in the form of its active derivative such as acid halide, acid anhydride or acid-lower alkyl ester; or the alcohol is reacted in the form or its active derivative such as lower carboxylic acid ester.

In the case where a carboxylic acid is used, the esterification reaction is carried out in an inert solvent in the presence of an acid catalyst. Examples of the acid catalyst include sulfuric acid, p-toluenesulfonic acid, and strongly acidic ion exchange resin. Examples of the reaction solvent include aliphatic hydrocarbons such as n-pentane, n-hexane, and n-heptane; alicyclic hydrocarbons such as cyclohexane; and aromatic hydrocarbons such as benzene, toluene, and xylene. In order to increase the rate of ester formation, the water formed by the reaction is discharged from the reaction system by azeotropy using an inert solvent.

In the case where an acid-lower alkyl ester is used, the ester exchange reaction is carried out in an inert organic solvent in the presence of a strong base under heating, while discharging the lower alcohol formed by the reaction from the reaction system. Examples of the reaction solvent include amides such as dimethylformamide, dimethylacetamide, and hexamethylphosphonamide, and organic solvents such as toluene and dimethylsulfoxide. Examples of the strong base include strongly basic alkali metal compounds such as sodium methylate, sodium ethylate, potassium hydroxide, and sodium amide; and titanate compounds such as tetraisopropyl or tetrabutyl titanate. The reaction smoothly proceeds by heating at 30° to 180° C.

In the case where an acid halide is used, the reaction is carried out at 0° to 130° C., preferably 20° to 70° C., in the presence of a hydrogen halide acceptor in an inert solvent. Examples of the hydrogen halide acceptor include pyridine, triethylamine, dimethylaniline, and tetramethyl urea. Examples of the inert solvent include aliphatic hydrocarbons such as n-hexane and n-heptane; alicyclic hydrocarbons such as cyclohexane; aromatic hydrocarbons such as benzene and xylene; and ethers such as diethyl ether and tetrahydrofuran.

In the case where an acid anhydride is used, the reaction is carried out in an inert solvent, or is carried out with an excess of the acid anhydride in the absence of an inert solvent. Examples of the inert solvent include aromatic hydrocarbons such as benzene, toluene, and xylene; and ether compounds such as diethyl ether and tetrahydrofuran.

Phenol Derivatives Represented By Formula (III)

In the formula (III), $R^1$ and $R^2$ each is the same as defined in the formula (II), and $R^4$ and $R^5$ each is an alkylene having 1 to 4 carbon atoms such as methylene, ethylene, and ethylethylene. The most preferred example for $R^4$ is trimethylene and the most preferred example for $R^5$ is ethylene.

Z is an n-valent group.

One group of Z is a metal. Examples of the metal include sodium, potassium, calcium, magnesium, zinc, nickel, and aluminum.

Another group of Z is a hydrocarbon residue. Examples thereof include $C_1$-$C_{18}$ alkyl, $C_1$-$C_{10}$ alkylene, $C_3$-$C_{10}$ 3 to 4-valent aliphatic hydrocarbon residue (e.g., 1,2,3-propanetriyl, 2,2-dimethylbutane-1,1',1''-triyl, and neopentanetetrayl), phenyl, phenylene, and 1,3,5-benzenetriyl.

Further group of Z is a group containing sulfur atom(s). Examples thereof include —$R^a$—S—$R^b$— (wherein $R^a$ and $R^b$ each is a $C_1$-$C_{10}$ alkylene, preferably $R^a$ and $R^b$ each is —$CH_2CH_2$—).

Still another group of Z is a group containing nitrogen atom(s). Examples thereof include N$+$R$^c+_{\overline{3}}$ (wherein $R^c$ is a $C_1$-$C_{10}$ alkylene) and 2,2,6,6-tetramethyl-4-piperidyl.

Still further group of Z is a group containing oxygen atom(s). Examples thereof include —$R^d+OR^e+_{\overline{m}}$ (wherein m is an integer of 1 to 3; $R^d$ and $R^e$ each is a $C_2$-$C_3$ alkylene), O+$CH_2$—C($CH_2+)_3$, and sucrose from which the hydroxyl groups are removed.

Yet further group of Z is a group containing both nitrogen and oxygen atoms. Examples thereof include the group of the formula

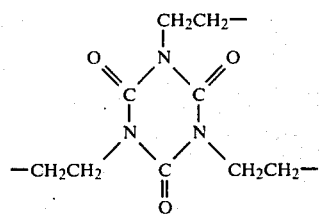

In formula (III), n is an integer of 1 to 8.

Representative examples of the phenol derivatives represented by the formula (III) are shown below. The numbers designating the compounds will be referred to in Examples described below.

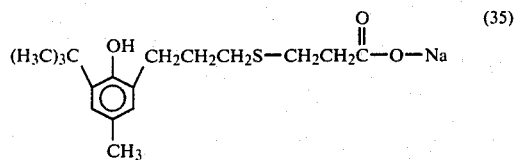

Sodium 3-[3-(3-tert-butyl-2-hydroxy-5-methylphenyl)-propylthio]propionate

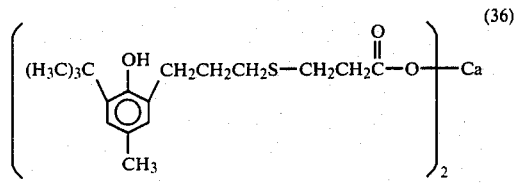

Calcium bis[3-[3-(3-tert-butyl-2-hydroxy-5-methylphenyl)propylthio]propionate]

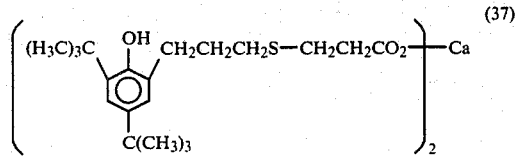

Calcium bis[3-[3-(3,5-di-tert-butyl-2-hydroxyphenyl)-propylthio]propionate]

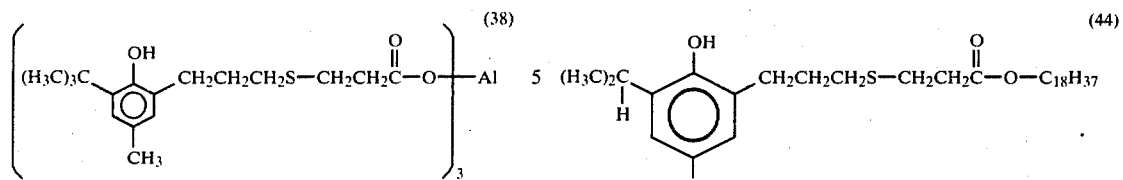

Aluminum tris[3-[3-(3-tert-butyl-2-hydroxy-5-methylphenyl)propylthio]propionate]     (38)

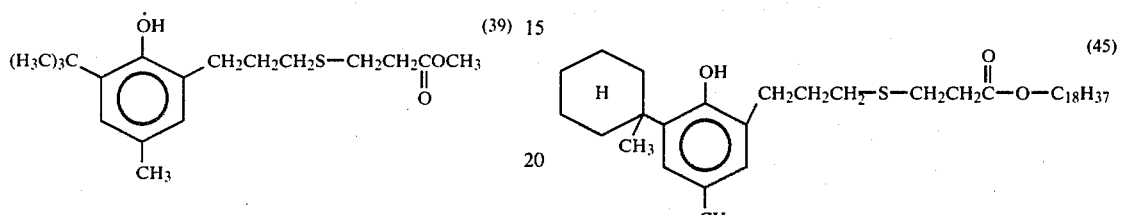

Methyl 3-[3-(3-tert-butyl-2-hydroxy-5-methylphenyl)propylthio]propionate     (39)

Methyl 3-[3-(3,5-di-tert-butyl-2-hydroxyphenyl)propylthio]propionate     (40)

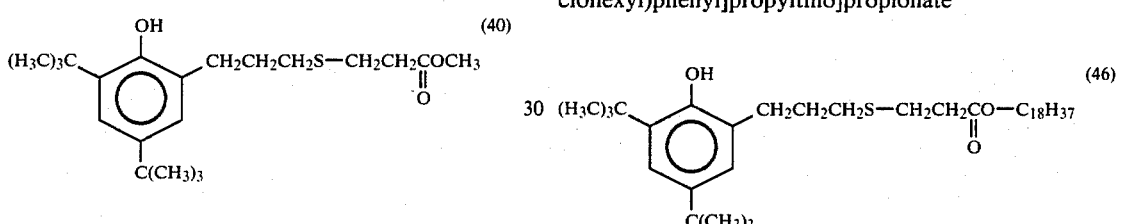

Methyl 3-[3-(2-hydroxy-5-methyl-3-(1-methylcyclohexyl)phenyl)propylthio]propionate     (41)

Ethyl 3-[3-(3-tert-butyl-2-hydroxy-5-methylphenyl)propylthio]propionate     (42)

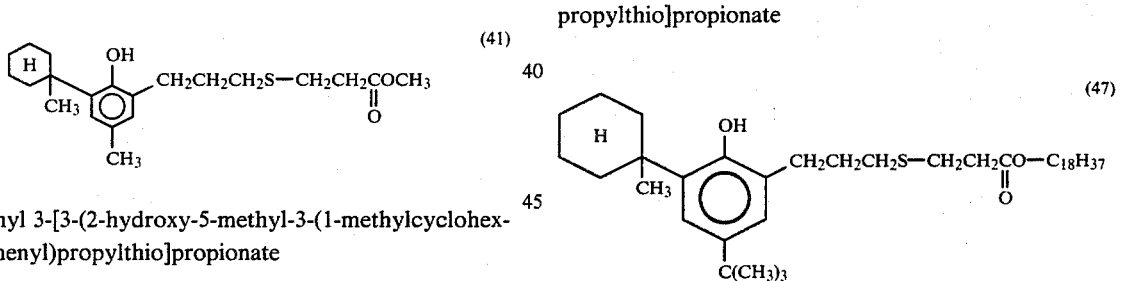

Octadecyl 3-[3-(3-tert-butyl-2-hydroxy-5-methylphenyl)propylthio]propionate     (43)

Octadecyl 3-[3-(2-hydroxy-3-isopropyl-5-methylphenyl)propylthio]propionate     (44)

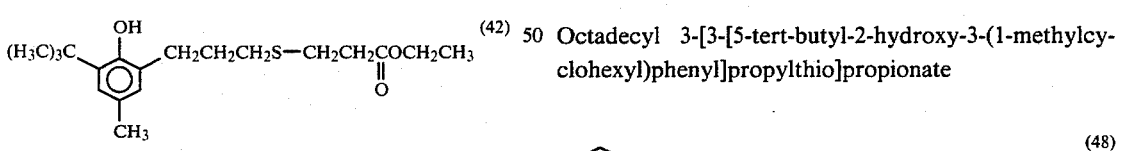

Octadecyl 3-[3-[2-hydroxy-5-methyl-3-(1-methylcyclohexyl)phenyl]propylthio]propionate     (45)

Octadecyl 3-[3-(3,5-di-tert-butyl-2-hydroxyphenyl)propylthio]propionate     (46)

Octadecyl 3-[3-[5-tert-butyl-2-hydroxy-3-(1-methylcyclohexyl)phenyl]propylthio]propionate     (47)

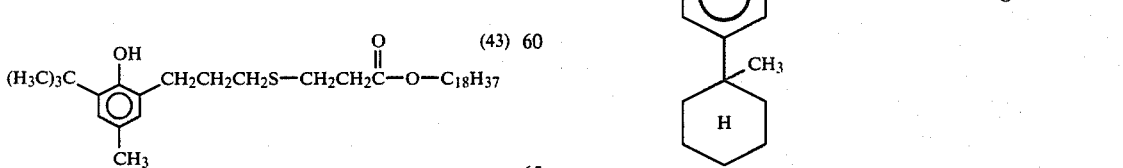

Octadecyl 3-[3-[2-hydroxy-3,5-bis(1-methylcyclohexyl)phenyl]propylthio]propionate     (48)

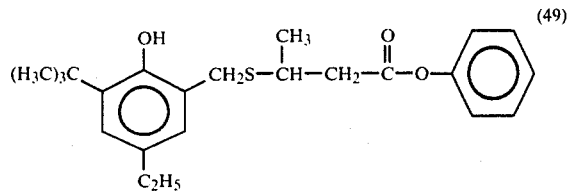

Phenyl 3-(3-tert-butyl-5-ethyl-2-hydroxyphenylmethyl-thio)butyrate

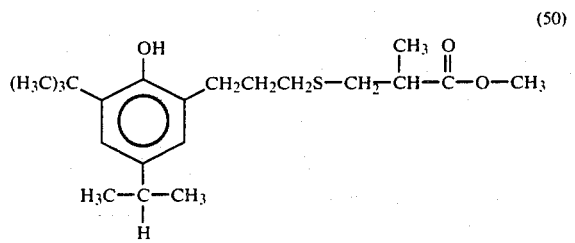

Methyl 3-[3-(3-tert-butyl-2-hydroxy-5-isopropyl-phenyl)propylthio]-2-methylpropionate

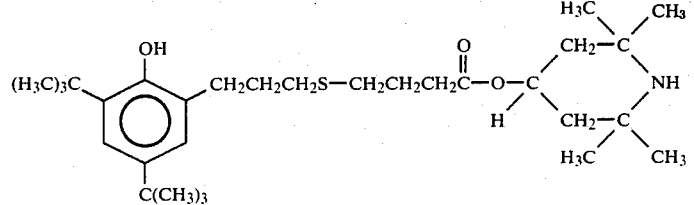

2,2,6,6-tetramethyl-4-piperidinyl 4-[3-(3,5-di-tert-butyl-2-hydroxyphenyl)propylthio]butyrate

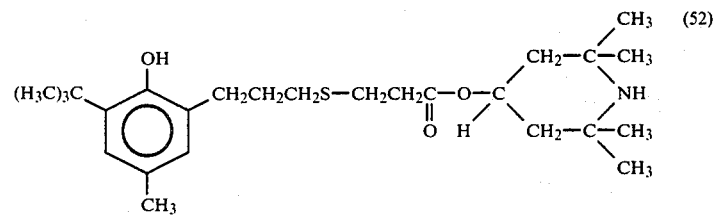

2,2,6,6-tetramethyl-4-piperidinyl 3-[3-(3-tert-butyl-2-hydroxy-5-methylphenyl)propylthio]propionate

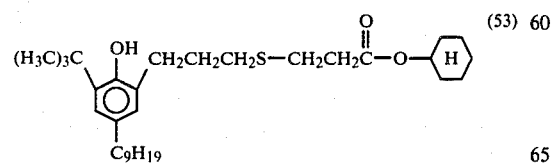

Cyclohexyl 3-[3-(3-tert-butyl-2-hydroxy-5-nonyl-phenyl)propylthio]propionate

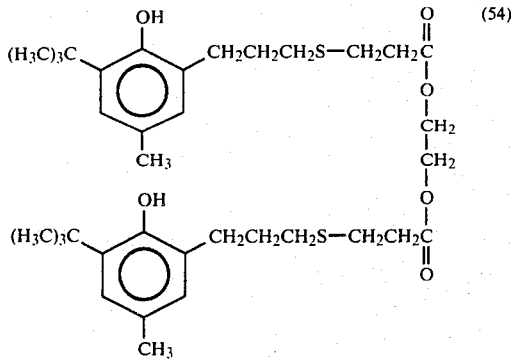

Ethylene bis[3-[3-(3-tert-butyl-2-hydroxy-4-methyl-phenyl)propylthio]propionate]

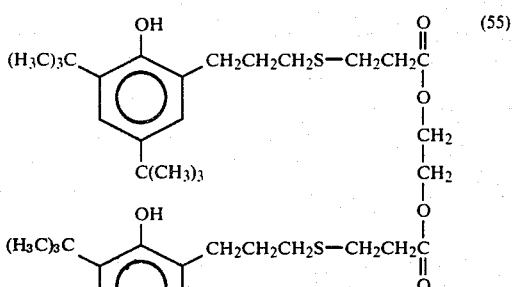
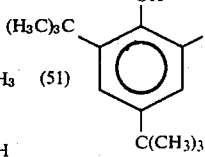

Ethylene bis[3-[3-(3,5-di-tert-butyl-2-hydroxyphenyl)-propylthio]propionate]

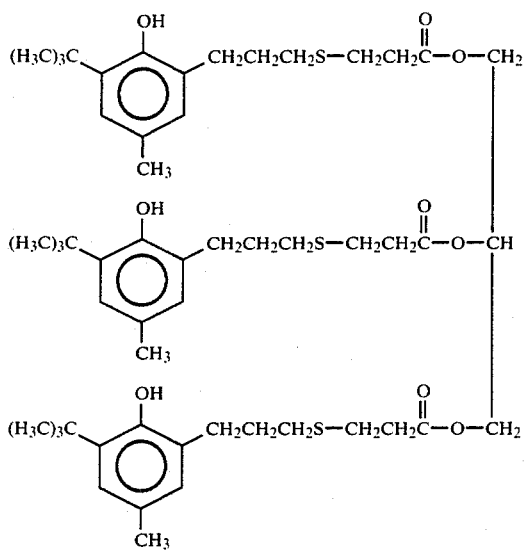

1,2,3-tris[3-[3-(3-tert-butyl-2-hydroxy-5-methylphenyl)-propylthio]propionyloxy]propane

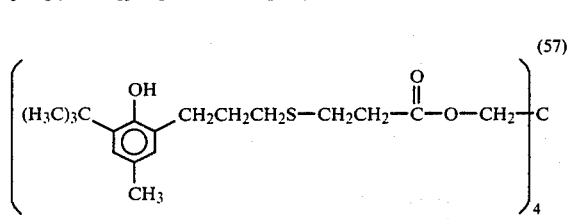

Tetrakis[3-[3-(3-tert-butyl-2-hydroxy-5-methylphenyl)-propylthio]propionyloxymethyl]methane

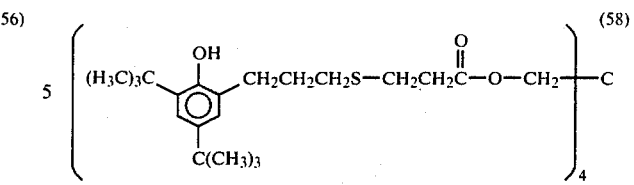

Tetrakis[3-[3-(3,5-di-tert-butyl-2-hydroxyphenyl)-propylthio]propionyloxymethyl]methane

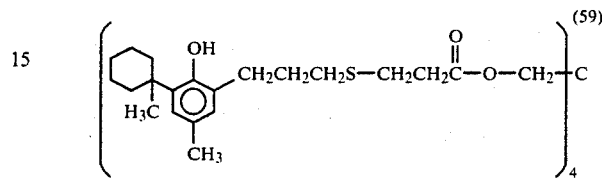

Tetrakis[3-[3-[2-hydroxy-5-methyl-3-(1-methylcyclohexyl)phenyl]propylthio]propionyloxymethyl]methane

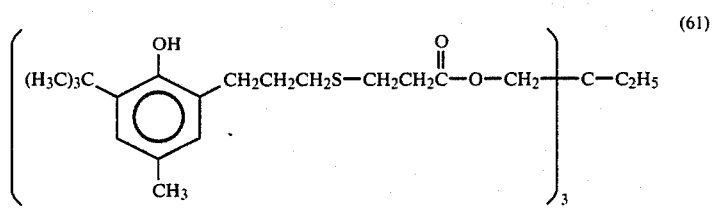

Tetrakis[3-[3-[2-hydroxy-3,5-bis(1-methylcyclohexyl)phenyl]propylthio]propionyloxymethyl]methane

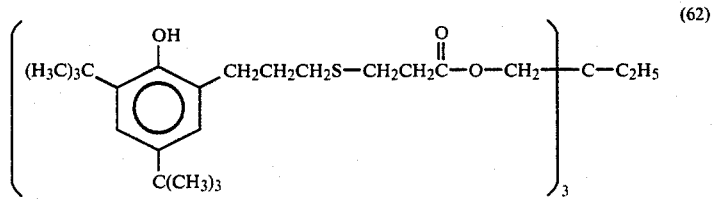

1,1,1-tris[3-[3-(3-tert-butyl-2-hydroxy-5-methylphenyl)-propylthio]propionyloxymethyl]propane 1,1,1-tris[3-[3-(3,5-di-tert-butyl-2-hydroxyphenyl)-propylthio]propionyloxymethyl]propane

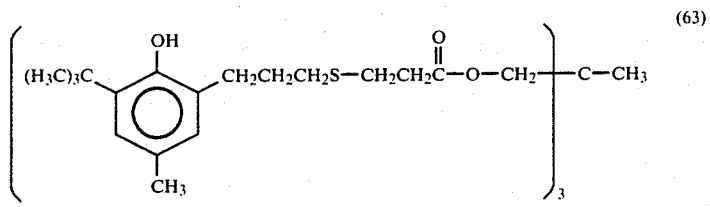

1,1,1-tris[3-[3-(3-tert-butyl-2-hydroxy-5-methylphenyl)-propylthio]propionyloxymethyl]ethane

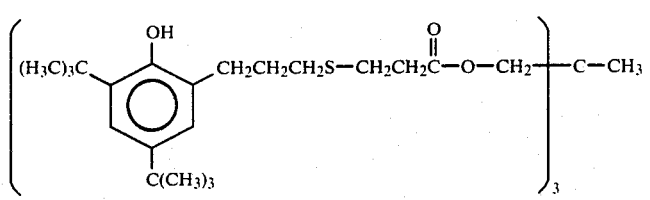

1,1,1-tris[3-[3-(3,5-di-tert-butyl-2-hydroxyphenyl)-propylthio]propionyloxymethyl]ethane

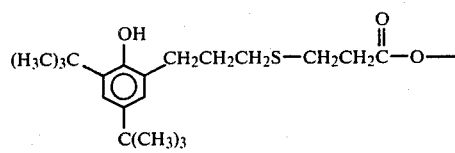

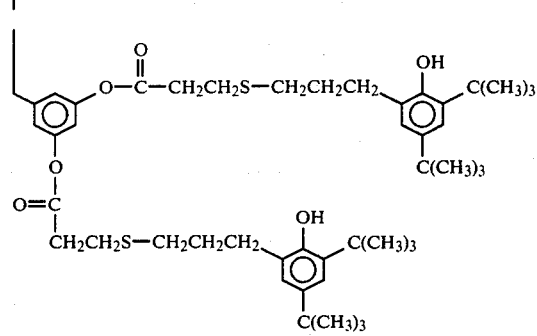

1,3,5-tris[3-[3-(3,5-di-tert-butyl-2-hydroxyphenyl)-propylthio]propionyloxy]benzene

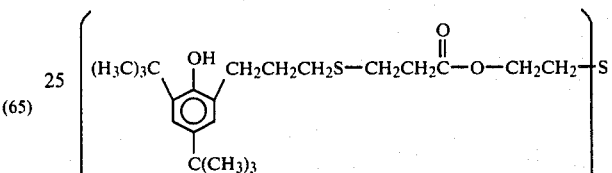

Bis[2-[3-[3-(3,5-di-tert-butyl-2-hydroxyphenyl)propyl-thio]propionyloxy]ethyl]sulfide

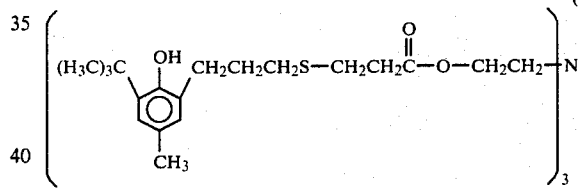

Tris[2-[3-[3-(3-tert-butyl-2-hydroxy-5-methylphenyl)-propylthio]propionyloxy]ethyl]amine

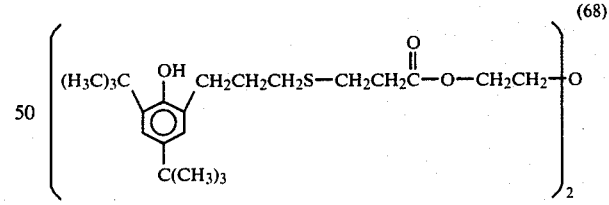

Bis[2-[3-[3-(3,5-di-tert-butylphenyl)propylthio]pro-pionyloxy]ethyl]ether

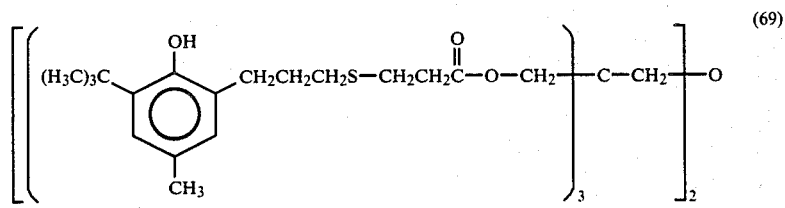

Bis[2,2,2-tris[3-[3-(3-tert-butyl-2-hydroxy-5-methyl-phenyl)propylthio]propionyloxymethyl]ethyl]ether

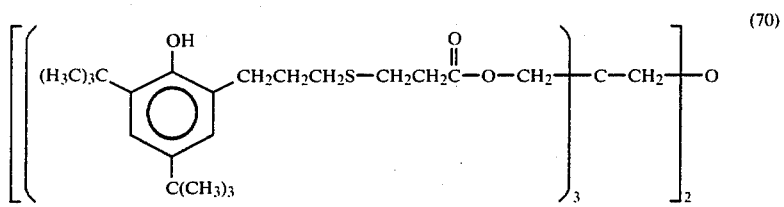

Bis[2,2,2-tris[3-[3-(3,5-di-tert-butyl-2-hydroxyphenyl)-propylthio]propionyloxymethyl]ethyl]ether

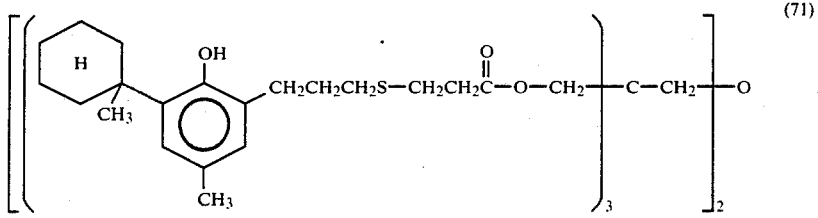

Bis[2,2,2-tris[3-[3-(2-hydroxy-5-methyl-3-(1-methylhexyl)phenyl]propylthio]propionyloxymethyl]ethyl]ether

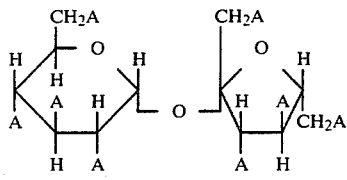

A:

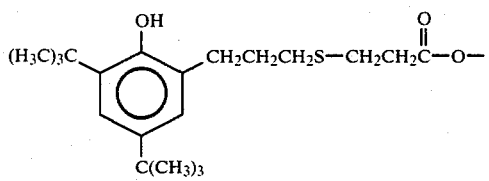

Octakisester of sucrose and 3-[3-(3,5-di-tert-butyl-2-hydroxyphenyl)propylthio]propionic acid

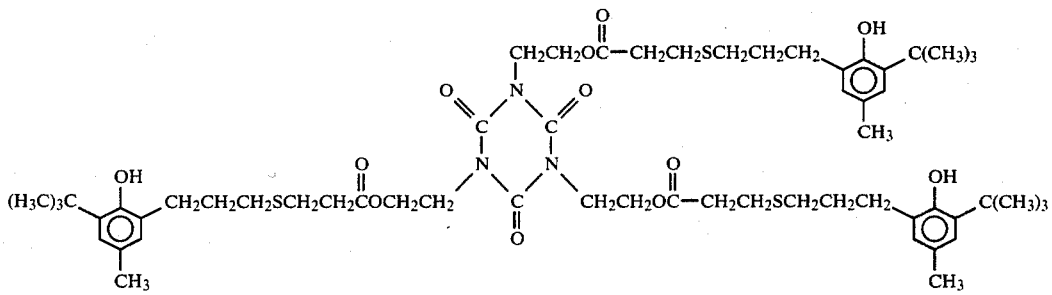

1,3,5-tris[2-[3-[3-(3-tert-butyl-2-hydroxy-5-methylphenyl)propylthio]propionyloxy]ethyl]-1,3,5-triazine-2,4,6(1H,3H,5H)-trione

Synthesis of Phenol Derivatives Represented By Formula (III)

The compound (III) of this invention can be produced in any manner by introducing or forming specific groups or linkages, as exemplified below.

(1) In the case where Z is a metal, the compound can be produced by reacting a hydroxide, carbonate or bicarbonate containing the metal with a carboxylic acid represented by formula (VI)

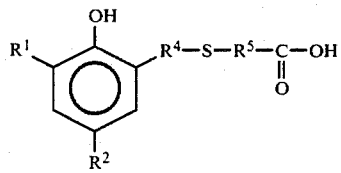

wherein $R^1$ is a secondary or tertiary hydrocarbon group residue having 3 to 8 carbon atoms; $R^2$ is a hydrocarbon residue having 1 to 12 carbon atoms; and $R^4$ and $R^5$ each is an alkylene group having 1 to 4 carbon number 1 to 4.

The reaction to synthesize a metal salt of carboxylic acid is carried out at 0° to 100° C., preferably 10° to 40° C., in water or an inert organic solvent. Examples of the inert organic solvent include polar solvents such as dimethylformamide, dimethylacetamide, hexamethylphosphonamide, and dimethylsulfoxide.

(2) In the case where Z is an organic group, the compound can be produced by reacting a compound represented by the formula (VII)

$(HO)_{\overline{n}}Z$     (VII)

wherein n is an integer of 1 to 8, with a carboxylic acid represented by the formula (VI) above or an active derivative thereof (acid-lower alkyl ester, acid halide, or acid anhydride).

The esterification reaction using a carboxylic acid is carried out in an inert organic solvent in the presence of an acid catalyst, or in excess of the compound of the formula (VII) in the absence of an inert organic solvent. Examples of the acid catalyst include sulfuric acid, p-toluenesulfonic acid, and strongly acidic ion exchange resin. Examples of the inert organic solvent include aliphatic hydrocarbons such as n-pentane, n-hexane, and n-heptane; alicyclic hydrocarbons such as cyclohexane; and aromatic hydrocarbons such as benzene, toluene, and xylene. In the case where an inert organic solvent is used, the water formed by the reaction is discharged from the reaction system by azeotropy using an inert organic solvent to increase the rate of ester formation.

The ester exchange reaction using an acid-lower alkyl ester is carried out under heating in an inert organic solvent in the presence of a strong base, while discharging the lower alcohol formed by the reaction from the reaction system. Examples of the inert organic solvent include amides such as dimethylformamide, dimethylacetamide or hexamethylphosphonamide, and organic solvents such as toluene or dimethylsulfoxide. Examples of the strong base include strongly basic alkali metal compounds such as sodium methylate, sodium ethylate, potassium hydroxide or sodium amide, and titanate compounds such as tetraisopropyl or tetrabutyl titanate. The reaction is suitably carried out by heating at 30° to 180° C.

The reaction using an acid halide is carried out at 0° to 130° C., preferably 20° to 70° C., in an inert solvent in the presence of a hydrogen halide acceptor. Examples of the hydrogen halide acceptor include pyridine, triethylamine, dimethylaniline, and tetramethyl urea. Examples of the inert solvent include aliphatic hydrocarbons such as n-hexane or n-heptane; alicyclic hydrocarbons such as cyclohexane; aromatic hydrocarbons such as benzene, toluene or xylene; and ether compounds such as diethyl ether or tetrahydrofuran.

The esterification reaction using an acid anhydride is carried out in an inert solvent, or in excess of the acid anhydride in the absence of an inert solvent. Examples of the inert solvent include aromatic hydrocarbons such as benzene, toluene or xylene; and ether compounds such as diethyl ether or tetrahydrofuran.

Application of the Compound

The phenol derivative of this invention represented by the formula (I) is effective to prevent the oxidation of organic materials as described below.

The phenol derivative of this invention as an antioxidant is effective to various organic materials. It is particularly useful when such is added to synthetic high molecular weight materials.

The amount of the phenol derivative of this invention as an antioxidant varies depending on the type, nature, and purpose of use of the organic materials such as rubber or resin to be stabilized. The amount is generally about 0.001 to 10 wt% based on the weight of the organic material. For most applications, it is used in an amount of about 0.01 to about 5 wt%. For example, 0.01 to 2.0 wt% for polyolefins, 0.01 to 1.0 wt% for polyvinyl chloride and polyvinylidene chloride, 0.1 to 2.0 wt% for polyethers, 0.3 to 3 wt% of polyurethane, and 0.01 to 1.0 wt% for polyester and polyamide.

The phenol derivative of this invention represented by the formula (I) is sufficiently effective as an antioxidant even when it is used alone, but the effect can be enhanced when used in combination with other antioxidants such as sulfur type antioxidant, phosphorus type antioxidant, phenol antioxidant, benzophenone type UV light absorber, benzotriazole type UV light absorber, hindered-amine type light stabilizer, organo-nickel type light stabilizer, metal type deactivator, filler deactivator or metal soap. It can also be used in the conventional manner in combination with adjuvants such as antistatic agent, flame retardant, anti-fogging agent, voltage stabilizer, crosslinking agent, slip agent or colorant.

The compounds obtained in the following Examples 1 to 17 are the phenol derivatives represented by the formula (II), and the compounds obtained in the following Examples 18 to 38 are the phenol derivatives represented by formula (III).

EXAMPLE 1

Bis[3-(3-tert-butyl-2-hydroxy-5-methylphenyl)-propyl]3,3'-thiodipropionate (Illustrative Compound No. 1)

Into a 30 ml four-neck flask equipped with a Dian-Stark trap were charged 1.28 g (7.20 mmol) of 3,3'-thiodipropionic acid, 4.00 g (17.99 mmol) of 3-(3-tert-butyl-2-hydroxy-5-methylphenyl)-1-propanol, 10 ml of toluene and 0.27 g (1.4 mmol) of p-toluenesulfonic acid hydrate, followed by heating and refluxing for 2 hours under a nitrogen stream. After the completion of the reaction, diethyl ether was added and the reaction product was washed with water. The reaction product was then washed with saturated aqueous solution of sodium chloride and dehydrated with anhydrous sodium sulfate. The organic solvent was removed under reduced pressure. After separation by silica gel column chromatography (solvent: chloroform), 2.67 g (4.55 mmol) of the desired product was obtained. The yield was 63%. The physical properties of the product are shown below.

(1) $^1$H-NMR CDCl$_3$ δ[ppm] 1.40 (18H, s), 2.25 (6H, s), 1.50–3.20 (16H, m), 4.10 (4H, t), 5.05 (2H, s), 6.72 (2H, d), 6.88 (2H, d).

(2) IR: NaCl wavenumber [cm$^{-1}$] 3500, 2950, 1720, 1595, 1440, 1170, 860.

(3) MS: m/e (relative intensity) 586 (10, M$^+$), 204 (100), 189 (70), 161 (20).

EXAMPLES 2 TO 9

The compounds as shown in Table 1 were synthesized according to the method used in Example 1. Their structures were confirmed by means of NMR spectrums, IR spectrums and MS spectrums.

TABLE 1

| Example | Reactants Carboxylic acid Compound of Formula (V) | (g) (mmol) | Alcohol Compound of Formula (IV) | (g) (mmol) | Reaction product Illustrated compound No. | Yield (g) (mmol) | Yield (%) | Physical properties of reaction product $^1$H—NMR CDCl$_3$ δ (ppm) | IR | MS |
|---|---|---|---|---|---|---|---|---|---|---|
| 2 | 3,3'-thiodi- | 1.08 | 3-(3,5-di-tert- | 4.00 | 4 | 3.91 | 96 | 1.31(18H,s) 1.54(18H,s), | 3500, 2950, | 670(1,M$^+$) |

TABLE 1-continued

| | Reactants | | | | Reaction product | | | Physical properties of reaction product | | |
|---|---|---|---|---|---|---|---|---|---|---|
| | Carboxylic acid | | Alcohol | | Illustrated | Yield | | | | |
| Example | Compound of Formula (V) | (g) (mmol) | Compound of Formula (IV) | (g) (mmol) | compound No. | (g) (mmol) | Yield (%) | $^1$H—NMR CDCl$_3$ δ (ppm) | IR | MS |
| | propionic acid | (6.05) | butyl-2-hydroxy-phenyl)-1-propanol | (15.1) | | (5.83) | | 1.60–2.40(4H,m), 2.40–3.30(12H,m), 4.17(4H,t), 4.90(2H,bs), 6.96(2H,d), 7.15(2H,d). | 1730, 1595, 1200, 880. | 246(30), 231(100). |
| 3 | Heptanedioic acid | 1.15 (7.20) | 3-(3-tert-butyl-2-hydroxy-5-methylphenyl)-1-propanol | 4.00 (17.99) | 11 | 3.00 (5.27) | 73 | 1.41(18H,s), 1.50–2.90 (18H,m), 2.25(6H,s), 4.10(4H,t), 5.05(2H,s), 6.75(2H,d), 6.90(2H,d). | 3490, 2940, 1720, 1595, 1200, 860. | 568(2,M$^+$) 204(100), 189(70), 161(30). |
| 4 | Diglycolic acid | 0.97 (7.20) | 3-(3-tert-butyl-2-hydroxy-5-methylphenyl)-1-propanol | 4.00 (17.99) | 12 | 2.72 (5.01) | 70 | 1.40(18H,s), 1.50–2.90 (8H,m), 2.23(6H,s), 4.24(4H,t), 4.24(4H,s), 4.70(2H,s), 6.75(2H,d), 6.90(2H,d). | 3540, 2940, 1740, 1590, 1210, 1120, 855. | 542 (0.1,M$^+$) 204(100), 189(85) 161(20). |
| 5* | Nitrilotriacetic acid | 1.03 (5.40) | 3-(3-tert-butyl-2-hydroxy-5-methylphenyl)-1-propanol | 4.50 (20.20) | 15 | 2.72 (3.38) | 63 | 1.40(27H,s), 1.50–2.90 (12H,m), 2.23(9H,s), 3.70(6H,s), 4.19(6H,t), 5.15(3H,bs), 6.75(3H,d), 6.90(3H,d). | 3500, 2950, 1740, 1595, 1260, 1090, 1100, 860, 800. | 806(10), 554(10), 204(60), 189(100), 161(35). |
| 6 | 1,2,3-propanetricarboxylic acid | 0.95 (5.40) | 3-(3-tert-butyl-2-hydroxy-5-methylphenyl)-1-propanol | 4.00 (17.99) | 16 | 2.90 (3.68) | 68 | 1.40(27H,s), 1.40–3.00 (17H,m), 2.21(9H,s), 4.17(6H,m), 5.04(2H,s), 5.30(1H,s), 6.70(3H,d), 6.88(3H,d). | 3500, 2950, 1720, 1595, 1170, 860. | 789(1,M$^+$) 204(100), 189(70), 177(20), 161(20), 149(20), 57(15). |
| 7 | Tetrakis(2-carboxyethyloxymethyl)methane | 1.72 (4.05) | 3-(3-tert-butyl-2-hydroxy-5-methylphenyl)-1-propanol | 4.00 (17.99) | 18 | 1.21 (0.97) | 24 | 1.40(36H,s), 1.50–2.90 (24H,m), 2.25(12H,s), 3.34(8H,s), 3.60(8H,t), 4.10(8H,t), 5.16(4H,s), 6.72(4H,d), 6.89(4H,d). | 3500, 2950, 1720, 1595, 1170, 1110, 860. | |
| 8 | Tris(2-carboxyethylthio)cyclododecane | 2.16 (4.50) | 3-(3-tert-butyl-2-hydroxy-5-methylphenyl)-1-propanol | 3.00 (13.49) | 27 | 2.19 (2.00) | 45 | 1.40(27H,s), 1.20–3.40 (39H,m), 2.25(9H,s), 4.15(6H,t), 5.00(3H,s), 6.74(3H,d), 6.87(3H,d). | 3480, 2950, 1730, 1590, 1270, 855. | |
| 9 | Tetrakis [3-(4-carboxybutylthio)-propionyloxymethyl]-methane | 2.91 (3.27) | 3-(3-tert-butyl-2-hydroxy-5-methylphenyl)-1-propanol | 4.37 (19.65) | 29 | 2.33 (1.36) | 42 | 1.40(36H,s), 1.10–3.40 (64H,m), 2.25(12H,s), 4.10(8H,t), 4.15(8H,s), 5.16(4H,s), 5.16(4H,s), 6.75(4H,d), 6.88(4H,d). | 3500, 2940, 1730, 1590, 1170, 855. | |

*Hydrated p-toluenesulfonic acid was used in an amount of 2.46 g (12.95 mmol), which is not a catalytic amount, so that all of it is not caught by nitrilotriacetic acid.
IR: KBr tablet or NaCl; wavenumber (cm$^{-1}$)
MS: m/e (relative intensity)

EXAMPLE 10

1,3,5-tris[3-(3-tert-butyl-2-hydroxy-5-methylphenyl)-propoxycarbonyl]benzene (Illustrative Compound No. 20)

Into a 100 ml reactor equipped with a condenser, thermometer and nitrogen introducing thin tube were charged 1.54 g (6.00 mmol) of trimethyl 1,3,5-benzenetricarboxylate, 4.00 g (18.00 mmol) of 3-(3-tert-butyl-2-hydroxy-5-methylphenyl)-1-propanol and 20 ml of N,N-dimethylformamide. The pressure of the reaction system was reduced to 20 mmHg and 75 vol% (15 ml) of N,N-dimethylformamide was distilled away to dry the reactants, solvent and apparatus. The reaction system was cooled to room temperature, and the vacuum was broken by introducing dry nitrogen. 0.07 g (1.8 mmol) of sodium amide was immediately added to initiate the ester exchange reaction. The reaction system was heated at 50° to 60° C. under 20 mmHg for 2 to 3 hours, and then heated at 60° to 80° C. under 20 mmHg for 2 to 3 hours while distilling N,N-dimethylformamide. Thereafter, the reaction mixture was further heated at 100° to 120° C. under 5 mmHg for 2 to 3 hours. When the reaction was completed, the reaction product was neutralized with dilute hydrochloric acid and then chloroform was added. After liquid separation and dehydration with anhydrous sodium sulfate, the organic solvent was removed under reduced pressure. After separation by silica gel chromatography (solvent: chloroform), 2.60 g (3.16 mmol) of the desired product was obtained. The yield was 53%. The physical properties of the product are shown below.

(1) $^1$H-NMR CDCl$_3$ δ[ppm]1.40 (27H, s), 1.80–3.10 (12H, m), 2.23 (9H, s), 4.40 (6H, t), 5.05 (3H, s), 6.78 (3H, d), 6.87 (3H, d), 8.76 (3H, s).

(2) IR: NaCl wavenumber [cm$^{-1}$] 3490, 2940, 1725, 1600, 1240, 850, 735.

EXAMPLES 11 TO 16

The compounds as shown in Table 2 were synthesized according to the method used in Example 10. Their structures were confirmed by means of NMR spectrums, IR spectrums and MS spectrums.

TABLE 2

| Example | Reactants Methyl carboxylate Compound of Formula (a) | (g) (mmol) | Alcohol Compound of Formula (IV) | (g) (mmol) | Reaction product Illustrated compound No. | Yield (g) (mmol) | Yield (%) | Physical properties of reaction product $^1$H—NMR CDCl$_3$ δ(ppm) | IR | MS |
|---|---|---|---|---|---|---|---|---|---|---|
| 11 | Tetramethyl 1,2,4,5-benzenetetracarboxylate | 1.72 (5.00) | 3-(3-tert-butyl-2-hydroxy-5-methylphenyl)-1-propanol | 4.45 (20.00) | 21 | 2.50 (2.33) | 47 | 1.40(36H,s) 1.80–3.00 (16H,m), 2.21(12H,s), 4.40(8H,t), 5.25(4H,s), 6.75(4H,d), 6.86(4H,d), 8.06(2H,d). | 3510, 2940, 1720, 1590, 1250, 855. | |
| 12 | 1,3,5-tris-[3-[2-(methoxycarbonyl)-ethylthio]-propyl]-1,3,5-triazine-2,4,6 (1H, 3H, 5H)—trione | 3.66 (6.00) | 3-(3-tert-butyl-2-hydroxy-5-methylphenyl)-1-propanol | 4.00 (17.99) | 22 | 2.97 (2.52) | 42 | 1.40(27H,s), 1.60–3.20 (36H,m), 2.25(9H,s), 3.80–4.40(12H,m), 5.05 (3H,s), 6.75(3H,d), 6.86(3H,d). | 3500, 2950, 1730, 1690, 1590, 1220, 1170, 860. | |
| 13 | 1,3,5-tris-[3-[2-(methoxycarbonyl)-ethylthio]-propyl]-1,3,5-triazine-2,4,6 (1H, 3H, 5H)—trione | 3.66 (6.00) | 3-[2-hydroxy-3-(1-methylcyclohexyl)-5-methylphenyl]-1-propanol | 4.72 (18.00) | 23 | 3.44 (2.64) | 44 | 1.30(9H,s), 1.27–3.17 (66H,m), 2.23(9H,s), 3.8–4.40(12H,m), 5.43 (3H,s), 6.67(3H,d), 6.87(3H,d). | 3500, 2950, 1730, 1690, 1590, 1220, 1170, 855. | |
| 14 | 2 or 3,5 or 6-bis[2-(methoxycarbonyl)ethylthio]-bicyclo-[2.2.1]-heptane | 5.94 (17.88) | 3-(3-tert-butyl-2-hydroxy-5-methylphenyl)-1-propanol | 7.95 (35.76) | 25 | 8.93 (12.52) | 70 | 1.03(18H,s), 2.13(6H,s), 1.02–3.20(26H,m), 4.05(4H,t), 5.00(2H,s), 6.70(2H,d), 6.85(2H,d). | 3500, 2900 1730, 1590, 855. | |
| 15 | Bis[2-[2,4-bis(methoxycarbonyl)-butylthio]-ethyl]ether | 5.51 (11.40) | 3-(3-tert-butyl-2-hydroxy-5-methylphenyl)-1-propanol | 12.70 (57.10) | 31 | 3.30 (2.65) | 23 | 1.27(36H,s), 2.10(12H,s), 1.10–3.10(34H,m), 3.50 (4H,t), 4.10(8H,m), 4.90(2H,s), 5.03(2H,s), 6.67(4H,d), 6.82(4H,d). | 3500, 2900 1730, 1590, 1160, 855. | |
| 16 | Bis[2,4-bis-(ethoxycarbonyl)butyl]-sulfide | 2.20 (5.10) | 3-[2-hydroxy-3-(1-methylcyclohexyl)-5-methylphenyl]-1-propanol | 5.00 (22.50) | 32 | 2.90 (2.50) | 49 | 1.45(36H,s), 1.70–3.00 (30H,m), 2.29(12H,s), 4.00–4.45(8H,m), 5.16 (4H,s), 6.80(4H,s), 6.95(4H,s). | 3500, 2950, 2860, 1730, 1590, 1480, 1190, 1125, 875. | |

Formula (a)

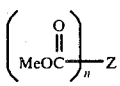

IR: KBr tablet or NaCl; wavenumber (cm$^{-1}$)
MS: m/e (relative intensity)

EXAMPLE 17

3-(3-tert-butyl-2-hydroxy-5-methylphenyl)propyl 3-[3-[2-(3,5-di-tert-butyl-4-hydroxyphenyl)ethylcarbonyloxy]propylthio]propionate (Illustrative Compound No. 14)

Into a 50 ml reactor were charged 3.40 g (15.29 mmol) of 3-(3-tert-butyl-2-hydroxy-5-methylphenyl)-1-propanol, 20 ml of diethyl ether and 1.94 g (16.00 mmol) of N,N-dimethylaniline. The atmosphere in the reactor was replaced with dry nitrogen. To the reactants was added dropwise 7.09 g (16.00 mmol) of 3-[3-[3-(3,5-di-tert-butyl-4-hydroxyphenyl)propionyloxy]propylthio]-propionyl chloride. The reactants were heated and refluxed for 6 hours in the nitrogen stream. After the completion of the reaction, diethyl ether was added and the reaction product was neutralized with 10% sulfuric acid. After liquid separation, washing with saturated aqueous solution of sodium chloride and dehydration with anhydrous sodium sulfate, the organic solvent was removed under reduced pressure. After separation by silica gel chromatography (solvent: chloroform), 6.42 g (10.20 mmol) of the desired product was obtained. The yield was 67%. The physical properties of the product are shown below.

(1) $^1$H-NMR CDCl$_3$ δ[ppm] 1.30 (27H, s), 1.50–2.30 (4H, s), 2.13 (3H, s), 2.30–3.00 (12H, m), 4.06 (4H, t), 4.95 (1H, s), 5.03 (1H, s), 9.67 (1H, d), 9.87 (1H, d), 9.88 (2H, s).

(2) IR: NaCl wavenumber [cm$^{-1}$] 3630, 3500, 2940, 1730, 1590, 1230, 1160, 870.

(3) MS: m/e (relative intensity) 628 (5, M$^+$), 424 (10), 204 (100), 189 (40), 161 (10), 147 (15), 57 (30).

The following Application Examples 1 to 16 demonstrate the antioxidant action of the compound (II) of this invention.

APPLICATION EXAMPLES 1 TO 11 AND COMPARATIVE APPLICATION EXAMPLES 1 TO 3

0.10 wt% of the antioxidant as shown in Table 3 was added to a polypropylene powder having an intrinsic viscosity of 1.9 (measured in tetralin at 135° C.) and an isotactic index of 98%, followed by thorough mixing by a mixer. The polypropylene powder was pelletized by melt mixing using a 20 mm diameter extruder (L/D: 20) at a cylinder temperature of 260° C. The MFR (at 230° C.) of the pellets was measured according to JIS K6758. The measured value was designated as $MFR_1$. The pelletizing process was repeated three times under the same conditions as above, and the MFR (at 230° C.) of the resulting pellets was measured. The measured value was designated as $MFR_4$. The results are shown in Table 3.

MFR is an index for the molecular weight, and the greater the MFR, the lower the molecular weight. The fact that both $MFR_1$ and $MFR_4$ were low and the difference therebetween was low indicates that the decrease of the molecular weight due to oxidative degradation in the extruder was small. This means that the antioxidant worked effectively.

TABLE 3

| Application Example | Illustrative Compound No. | Comparative Example | Antioxidant | $MFR_1$ | $MFR_4$ |
|---|---|---|---|---|---|
| | | 1 | None | 12.5 | 50 or more |
| | | 2 | 4,4'-butylidenebis(2-tert-butyl-5-methylphenol) | 7.2 | 13.5 |
| | | 3 | Tetrakis[3-(3,5-di-tert-butyl-4-hydroxyphenyl)propionyloxymethyl]methane | 6.5 | 12.2 |
| 1 | 1 | | Bis[3-(3-tert-butyl-2-hydroxy-5-methylphenyl)propyl]3,3'-thiodipropionate | 4.0 | 6.3 |
| 2 | 4 | | Bis[3-(3,5-di-tert-butyl-2-hydroxyphenyl)propyl] 3,3'-thiodipropionate | 4.6 | 8.7 |
| 3 | 16 | | Tris[3-(3-tert-butyl-2-hydroxy-5-methylphenyl)propyl] 1,2,3-propanetricarboxylate | 3.8 | 5.2 |
| 4 | 15 | | Tris[3-(3-tert-butyl-2-hydroxy-5-methylphenyl)propoxycarbonylmethyl]amine | 4.2 | 6.1 |
| 5 | 18 | | Tetrakis[2-[3-(3-tert-butyl-2-hydroxy-5-methylphenyl)propoxycarbonl]ethyloxymethyl]methane | 3.8 | 5.5 |
| 6 | 20 | | 1,3,5-tris[3-(3-tert-butyl-2-hydroxy-5-methylphenyl)propoxycarbonyl]benzene | 3.8 | 5.2 |
| 7 | 21 | | 1,2,4,5-tetrakis[3-(3-tert-butyl-2-hydroxy-5-methylphenyl)propoxycarbonyl]benzene | 3.9 | 5.5 |
| 8 | 22 | | 1,3,5-tris[3-[2-[3-(3-tert-butyl-2-hydroxy-5-methylphenyl)propoxycarbonyl]ethylthio]propyl]-1,3,5-triazine-2,4,6 (1H, 3H, 5H)-trione | 3.4 | 4.2 |
| 9 | 23 | | 1,3,5-tris[3-[2-[3-(2-hydroxy-3-(1-methylcyclohexyl)-5-methylphenyl)propyloxycarbonyl]ethylthio[propyl]-1,3,5-triazine-2,4,6(1H, 3H, 5H)-trione | 3.4 | 4.2 |
| 10 | 27 | | Tris[2-[3-(3-tert-butyl-2-hydroxy-5-methylphenyl)propoxycarbonyl]ethylthiol]cyclodecane | 3.5 | 4.5 |
| 11 | 29 | | Tetrakis[3-[4-[3-(tert-butyl-2-hydroxy-5-methylphenyl)propoxycarbonyl]butylthio]propionyloxymethyl]methane | 3.5 | 4.6 |

APPLICATION EXAMPLES 12 TO 16 AND COMPARATIVE APPLICATION EXAMPLES 4 TO 8

0.10 wt% of the antioxidant as shown in Table 4 was added to a powder of propylene-ethylene block copolymer having an intrinsic viscosity of 2.3 (measured in tetralin at 135° C.) and containing 13 wt% of ethylene, followed by thorough mixing using a mixer. The powder was pelletized by melt mixing using a 20 mm diameter extruder (L/D: 20) at a cylinder temperature of 260° C. The pellets were formed into a 0.5 mm thick sheet by compression molding at 230° C. The test piece was heated at 150° C. in a circulating air oven. The time required for the test piece to color brown due to oxidative degradation was measured. The results are shown in Table 4.

TABLE 4

| Application Example | Illustrative Compound No. | Comparative Example | Antioxidant | Thermal Aging Resistance (hours) |
|---|---|---|---|---|
| | | 4 | None | 0.5 or less |
| | | 5 | 2,6-di-tert-butyl-4-methylphenol | 1 or less |
| | | 6 | 2,2'-methylenebis(6-tert-butyl-4-methylphenol) | 17 |
| | | 7 | 4,4'-butylidenbis(2-tert-butyl-5-methylphenol) | 16 |
| | | 8 | 1,1,3-tris(5-tert-butyl-4-hydroxy-2-methylphenyl)-butane | 36 |
| 12 | 1 | | Bis[3-(3-tert-butyl-2-hydroxy-5-methylphenyl)propyl] 3,3'-thiodipropionate | 283 |
| 13 | 4 | | Bis[3-(3,5-di-tert-butyl-2-hydroxyphenyl)propyl] 3,3'-thiodipropionate | 284 |
| 14 | 16 | | Tris[3-(3-tert-butyl-2-hydroxy-5-methylphenyl)propyl] 1,2,3-propanetricarboxylate | 208 |
| 15 | 27 | | Tris[2-[3-(3-tert-butyl-2-hydroxy-5-methylphenyl)propoxycarbonyl]ethylthio]cyclodecane | 388 |
| 16 | 21 | | 1,2,4,5-tetrakis[3-(3-tert-butyl-2-hydroxy-5-methyl- | 263 |

EXAMPLE 18

Calcium bis[3-[3-(3,5-di-tert-butyl-2-hydroxyphenyl)propylthio]-propionate](Illustrative Compound No. 37)

Into a 500 ml three-neck flask were charged 7.25 g (20.6 mmol) of 3-[3-(3,5-di-tert-butyl-2-hydroxyphenyl)propylthio]propionic acid, 0.76 g (10.3 mmol) of calcium hydroxide and 200 ml of water, followed by heating and refluxing for about 5 hours.

After the completion of the reaction, water was distilled away and the residual white solids were washed with a small amount of methanol. Thus, 7.65 g (10.3 mmol) of the desired product was obtained. The yield was 100%. The physical properties of the product are shown below.

(1) Melting point: 230° C.
(2) $^1$H-NMR CDCl$_3$ δ[ppm] 1.28 (9H, s), 1.42 (9H, s), 1.95 (2H, tt), 2.40–3.09 (8H, m), 6.95 (1H, d), 7.13 (1H, d).
(3) IR: KBr tablet, wavenumber [cm$^{-1}$] 3400, 2950, 1550, 1440, 1410, 1190, 870.

EXAMPLE 19

Methyl 3-[3-(3-tert-butyl-2-hydroxy-5-methylphenyl)propylthio]propionate (Illustrative Compound No. 39)

Into a 1 liter four-neck flask were charged 50.00 g (161.1 mmol) of 3-[3-(3-tert-butyl-2-hydroxy-5-methylphenyl)propylthio]propionic acid and 500 ml of methanol. After complete dissolution, 1 ml of conc. sulfuric acid was added. The atmosphere in the reactor was replaced with dry nitrogen, and the reactants were heated and refluxed for about 5 hours.

After the completion of the reaction, methanol was removed under reduced pressure. After separation by silica gel chromatography (solvent: chloroform), 49.63 g (153.0 mmol) of the desired product was obtained. The yield was 95%. The physical properties of the product are shown below.

(1) $^1$H-NMR CDCl$_3$ δ[ppm] 1.40 (9H, s), 1.95 (2H, tt), 2.23 (3H, s), 2.50–3.10 (8H, m), 3.66 (3H, s), 5.42 (1H, s), 6.72 (1H, d), 6.89 (1H, d).
(2) IR * NaCl, wavenumber [cm$^{-1}$] 3500, 2950, 1740, 1595, 1440, 1220, 1170, 1020, 860, 765.
(3) MS: m/e (relative intensity) 324 (30, M$^+$), 204 (50), 189 (100), 161 (30).

EXAMPLES 20 TO 22

The compounds as shown in Table 5 were synthesized according to the method used in Example 19. Their structures were confirmed by means of NMR spectrums, IR spectrums and MS spectrums.

TABLE 5

| Example | Reactants: Compound of Formula (VII) | (ml) | Compound of Formula (VI) | (g) (mmol) | Reactions product: Illustrated compound No. | Yield (g) (mmol) | Yield (%) | $^1$H—NMR CDCl$_3$ δ (ppm) | IR NaCl wavenumber (cm$^{-1}$) | MS m/e relative intensity |
|---|---|---|---|---|---|---|---|---|---|---|
| 20 | Methanol | 500 | 3-[3-(3,5-di-tert-butyl-2-hydroxyphenyl)propylthio]propionic acid | 51.00 (144.7) | 40 | 49.52 (135.1) | 93 | 1.28(9H,s), 1.42(9H,s), 1.95(2H,tt), 2.40–3.09 (8H,m), 3.68(3H,s), 5.44 (1H,s), 6.95(1H,d), 7.13 (1H,d). | 3520, 2950, 1740, 1595, 1440, 1170, 1020, 880, 765. | 366(6,M$^+$), 351(3), 246(40), 231(100), 57(60). |
| 21 | Methanol | 500 | 3-[3-[2-hydroxy-5-methyl-3-(1-methylcyclohexyl)phenyl]propylthio]propionic acid | 45.00 (128.4) | 41 | 43.69 (119.7) | 93 | 1.25–2.20(10H,m), 1.33(3H,s), 1.91(4H,tt), 2.26(3H,s), 2.54–2.85 (8H,m), 3.71(3H,s), 5.56(1H,s), 6.77(1H,d), 6.96(1H,d). | 3500, 2900, 1730, 1590, 1440, 1350, 1245, 1195, 1160, 855, 760. | 364(5,M$^+$) 244(100), 299(40), 201(30), 175(20), 161(60), 147(40), 97(40), 55(50). |
| 22 | Ethanol | 500 | 3-[3-(3-tert-butyl-2-hydroxy-5-methylphenyl)propylthio]propionic acid | 50.00 (161.1) | 42 | 48.55 (143.4) | 89 | 1.23(H,t), 1.40(9H,s), 1.93(2H,tt), 2.23(3H,s), 1.36–3.00(8H,m), 4.13 (2H,q), 5.47(1H,s), 6.75(1H,d), 6.90(1H,d). | 3470, 2930, 1730, 1585, 1440, 1165, 1020, 885, 760. | |

EXAMPLE 23

Tetrakis[3-[3-(3-tert-butyl-2-hydroxy-5-methylphenyl)propylthio]propionyloxymethyl]methane (Illustrative Compound No. 57)

Into a 50 ml reactor equipped with a condenser, thermometer and nitrogen introducing thin tube were charged 11.00 g (33.90 mmol) of methyl 3-[3-(3-tert-butyl-2-hydroxy-5-methylphenyl)propylthio]propionate, 0.92 g (6.78 mmol) of pentaerythritol and 20 ml of N,N-dimethylformamide. The pressure in reaction system was reduced to 20 mmHg and 75 vol% (15 ml) of N,N-dimethylformamide was distilled away to dry the reactants, solvent and apparatus. The reaction system was cooled to room temperature, and the vacuum was broken by introducing dry nitrogen. 0.02 g (2.52 mmol) of lithium hydride was immediately added to initiate the ester exchange reaction. The reaction system was heated at 50° to 60° C. under 20 mmHg for 2 to 3 hours, and then heated at 60° to 80° C. under 20 mmHg for 2 to 3 hours while distilling N,N-dimethylformamide. Thereafter, the reaction mixture was further heated at 100° to 120° C. under 5 mmHg for 2 to 3 hours. When the reaction was completed, the reaction product was neutralized with dilute hydrochloric acid and then chloroform was added. After liquid separation and dehydration with anhydrous sodium sulfate, the organic solvent was removed under reduced pressure. After separation by silica gel column chromatography (solvent: chloroform), there was obtained 7.05 g (5.40 mmol) of the desired product. The yield was 80%. The physical properties of the product are shown below.

(1) $^1$H-NMR CDCl$_3$ δ[ppm] 1.39 (36H, s), 1.91 (8H, tt), 2.22 (12H, s), 2.36–3.01 (32H, m), 4.16 (8H, s), 5.42 (4H, s), 6.73 (4H, d), 6.90 (4H, d).

(2) IR: NaCl wavenumber [cm$^{-1}$]3500, 2930, 1735, 1595, 1440, 1214, 1165, 1020, 860, 750.

EXAMPLES 24 TO 38

The compounds as shown in Table 6 were synthesized according to the method used in Example 23. Their structures were confirmed by means of NMR spectrums, IR spectrums, MS spectrums and elemental analyses.

TABLE 6

| | | Reactants | | | Reaction product | | | | Physical properties of reaction product | | |
|---|---|---|---|---|---|---|---|---|---|---|---|
| Example | Compound of Formula (VII) | Methyl ester of Formula (VI) | (g) | (mmol) | Illustrated compound No. | Yield (g) | (mmol) | Yield (%) | $^1$H—NMR CDCl$_3$ δ (ppm) | IR NaCl wavenumber (cm$^{-1}$) | MS m/e relative intensity | Elemental analysis |
|---|---|---|---|---|---|---|---|---|---|---|---|---|
| 24 | Octadecanol 14.99 (55.42) | Methyl 3-[3-(3-tert-butyl-2-hydroxy-5-methylphenyl)-propylthio]-propionate | 9.00 | (27.74) | 43 | 14.23 | (25.28) | 91 | 0.70–2.20(37H,m), 1.37(9H,s), 2.23(3H,s), 2.35–3.00(8H,m), 4.06(2H,t), 5.47(1H,s), 6.72(1H,d), 6.86(1H,d) | 3490, 2900, 1730, 1590, 1460, 1355, 1170, 855, 760, 720. | | |
| 25 | Octadecanol 13.30 (49.17) | Methyl 3-[3-(3,5-di-tert-butyl-2-hydroxyphenyl)-propylthio]-propionate | 9.00 | (24.55) | 46 | 13.37 | (22.10) | 90 | 0.71–2.20(37H,m), 1.28(9H,s), 1.42(9H,s), 2.40–3.09(8H,m), 4.05(2H,t), 5.44(1H,s), 6.96(1H,s), 7.14(1H,d). | 3510, 2940, 1730, 1590, 1450, 1355, 1170, 860, 760. | | |
| 26 | Octadecanol 15.00 (55.45) | Methyl 3-[3-(5-tert-butyl-2-hydroxy-3-(1-methylcyclohexyl)phenyl]-propylthio]-propionate | | (27.73) | 47 | | (25.51) | 92 | 0.70–2.20(50H,m), 1.28(9H,s), 2.37–3.08(8H,m), 4.06(2H,t), 5.46(1H,s), 7.00(1H,d), 7.18(1H,d). | 3500, 2900, 1730, 1590, 1460, 1355, 1165, 860, 760. | | |
| 27 | Octadecanol 15.00 (55.45) | Methyl 3-[3-[2-hydroxy-3,5-bis(1-methylcyclohexyl)phenyl]propylthio]propionate | | (27.73) | 48 | | (26.34) | 96 | 0.69–2.20(63H,m), 2.36–3.05(8H,m), 4.05(2H,t), 5.45(1H,s), 7.01(1H,d), 7.19(1H,d). | 3510, 2900, 1730, 1590, 1450, 1355, 1170, 860, 765. | | |
| 28 | 2,2,6,6-tetramethyl-4-piperidinol 3.46 (22.00) | Methyl 3-[3-(3-tert-butyl-2-hydroxy-5-methylphenyl)-propylthio]-propionate | 7.14 | (22.00) | 52 | 3.50 | (7.78) | 35 | 0.90–2.20(18H,m), 1.40(9H,s), 2.21(3H,s), 2.30–3.01(8H,m), 5.20(1H,m), 5.50(1H,s), 6.71(1H,d), 6.89(1H,d). | 3500, 2950, 1730, 1590, 1440, 1360, 1240, 1170, 1010, 860, 765. | 449(10,M$^+$) 140(30) 124(100) | See Note 1 |
| 29 | Pentaery-thritol 1.85 (13.59) | Methyl 3-[3-(3,5-di-tert-butyl-2-hydroxyphenyl)propylthio]propionate | 19.94 | (54.40) | 58 | 16.03 | (10.87) | 90 | 1.31(36H,s), 1.45(36H,s), 2.00(8H,tt), 2.40–3.10(32H,m), 4.25(8H,s), 5.52(4H,s), 7.00(4H,d), 7.21(4H,d). | 3450, 2950, 1740, 1600, 1480, 1360, 1200, 1140, 1030, 880, 760. | | |
| 30 | Pentaery-thritol 0.93 (6.86) | Methyl 3-[3-[2-hydroxy-5-methyl-3-(1- | 10.00 | (27.43) | 59 | 7.65 | (5.22) | 76 | 0.8–2.3(48H,m), 1.30(12H,s), 2.20(12H,s), | 3500, 2900, 1735, 1590, 1160, 1020, | | |

TABLE 6-continued

| No. | Alcohol | g (mmol) | Ester | g (mmol) | Ex. | g (mmol) | Yield (%) | NMR | IR | Note |
|---|---|---|---|---|---|---|---|---|---|---|
| 31 | 2-ethyl-2-(hydroxymethyl)-1,3-propanediol | 1.15 (8.56) | Methyl 3-[3-(3-tert-butyl-2-hydroxy-5-methylphenyl)-propylthio]-propionate | 10.00 (30.82) | 61 | 5.00 (4.94) | 58 | 0.70–1.10(5H,m), 1.28(27H,s), 1.40(27H,s), 1.95(6H,t), 2.23(9H,s), 2.35–3.00(24H,m), 4.07(6H,s), 5.47(3H,s), 6.74(3H,d), 6.90(3H,d) | 3500, 2950, 1740, 1595, 1220, 1170, 1020, 860, 755. | |
| 32 | 2-ethyl-2-(hydroxymethyl)-1,3-propanediol | 1.02 (7.60) | Methyl 3-[3,5-di-tert-butyl-2-hydroxyphenyl)thio]propionate | 10.00 (27.28) | 62 | 7.10 (6.24) | 82 | 0.70–1.10(5H,m), 1.28(27H,s), 1.41(27H,s), 1.95(6H,t), 2.35–3.05(24H,m), 4.04(6H,s), 5.44(3H,s), 6.89(3H,d), 7.10(3H,d) | 3470, 2960, 1740, 1595, 1190, 1020, 880, 765, 725. | See Note 2 |
| 33 | 2-methyl-2-(hydroxymethyl)-1,3-propanediol | 1.20 (10.00) | Methyl 3-[3-(3-tert-butyl-2-hydroxy-5-methylphenyl)-propylthio]-propionate | 10.71 (33.00) | 63 | 6.00 (6.02) | 60 | 1.05(3H,s), 1.40(27H,s), 1.95(6H,t), 2.23(9H,s), 2.35–3.00(24H,m), 4.04(6H,s), 5.47(3H,s), 6.73(3H,d), 6.90(3H,d) | 3530, 2960, 1745, 1600, 1225, 1175, 1030, 865, 760. | See Note 3 |
| 34 | 2-methyl-2-(hydroxymethyl)-1,3-propanediol | 0.90 (7.49) | Methyl 3-[3,5-di-tert-butyl-2-hydroxyphenyl)thio]propionate | 10.00 (27.28) | 64 | 7.06 (6.28) | 84 | 1.04(3H,s), 1.29(27H,s), 1.42(27H,s), 1.95(6H,t), 2.40–3.05(24H,m), 4.05(6H,s), 5.46(3H,s), 6.93(3H,d), 7.14(3H,d) | 3430, 2950, 1740, 1600, 1190, 1020, 875, 760. | |
| 35 | dipentaerythritol | 1.09 (4.29) | Methyl 3-[3-(3-tert-butyl-2-hydroxy-5-methylphenyl)-propylthio]-propionate | 10.00 (30.82) | 69 | 6.60 (3.29) | 77 | 1.37(54H,s), 1.90(12H,t), 2.22(18H,s), 2.35–3.00(48H,m), 3.41(4H,s), 5.45(6H,s), 6.72(6H,d), 6.87(6H,d) | 3420, 2950, 1740, 1600, 1170, 1020, 860, 765. | See Note 4 |
| 36 | dipentaerythritol | 0.96 (3.78) | Methyl 3-[3,5-di-tert-butyl-2-hydroxyphenyl)propyl- | 10.00 (27.28) | 70 | 6.11 (2.70) | 71 | 1.30(54H,s), 1.41(54H,s), 1.98(12H,t), 2.35–3.00(48H,m), | 3470, 2940, 1730, 1590, 1180, 1020, 875, 750. | |

TABLE 6-continued

| | | | | thio]propionate | | | 3.45(4H,s),<br>4.17(12H,s),<br>5.49(6H,s),<br>6.95(6H,d),<br>7.16(6H,d). | |
|---|---|---|---|---|---|---|---|---|
| 37 | dipenta-<br>erythritol | 1.13<br>(4.45) | 14.60<br>(40.05) | Methyl 3-[2-hydroxy-5-methyl-3-(1-methylcyclo-hexyl)phenyl]-propylthio]-propionate | 71 | 4.45<br>(1.98) | 45 | 1.10–2.2(72H,m),<br>1.34(18H,s),<br>2.25(18H,s),<br>2.4–3.2(48H,m),<br>3.48(4H,s),<br>4.21(12H,s),<br>5.55(6H,s),<br>6.78(6H,d),<br>6.97(6H,d). | 3470, 2900,<br>1730, 1590,<br>1160, 1040,<br>850, 760. |
| 38 | 1,3,5-tris-(2-hydroxy-ethyl)-1,3,5-triazine-2,4,6(1H,3H,5H)-trione | 1.83<br>(7.01) | 8.18<br>(25.21) | Methyl 3-[3-tert-butyl-2-hydroxy-5-methylphenyl)-propylthio]-propionate | 73 | 4.94<br>(4.34) | 62 | 1.41(27H,s),<br>1.95(6H,t),<br>2.24(9H,s),<br>2.35–3.00(24H,m),<br>4.00–4.50(12H,m),<br>5.46(3H,s),<br>6.75(3H,d),<br>6.90(3H,d). | 3500, 2900,<br>1730, 1590,<br>1220, 1040,<br>855, 760. |

Note to Table 6:
(1) $C_{26}H_{43}NO_3S$
    Calcd.    Found
  C: 69.47%  69.44%
  H: 9.65%    9.64%
  N: 3.11%    3.11%
(2) $C_{66}H_{104}O_9S_3$
    Calcd.    Found
  C: 69.50%  69.68%
  H: 9.14%    9.21%
(3) $C_{56}H_{84}O_9S_3$
    Calcd.    Found
  C: 67.38%  67.43%
  H: 8.38%    8.49%
(4) $C_{112}H_{166}O_{19}S_6$
    Calcd.    Found
  C: 67.09%  66.96%
  H: 8.29%    8.33%

The following Application Examples 17 to 23 demonstrate the antioxidant action of the compound (III) of this invention.

APPLICATION EXAMPLES 17 TO 20

0.10 wt% of the antioxidant as shown in Table 7 was added to a polypropylene powder having an intrinsic viscosity of 1.9 (measured in tetralin at 135° C.) and an isotactic index of 98%, followed by thorough mixing using a mixer. The polypropylene powder was pelletized by melt mixing using a 20 mm diameter extruder (L/D: 20) at a cylinder temperature of 260° C. The MFR (at 230° C.) of the pellets was measured according to JIS K6758. The measured value was designated as $MFR_1$. The pelletizing process was repeated three times under the same conditions as above, and the MFR (at 230° C.) of the resulting pellets was measured. The measured value was designated as $MFR_4$. The results are shown in Table 7.

der was pelletized by melt mixing using a 20 mm diameter extruder (L/D: 20) at a cylinder temperature of 260° C. The pellets were formed into a 0.5 mm thick sheet by compression molding at 230° C. The test piece was heated at 150° C. in a circulating air oven. The time required for the test piece to color brown due to oxidative degradation was measured. The results are shown in Table 8.

TABLE 8

| Application Example | Illustrative Compound No. | Comparative Example | Antioxidant | Thermal Aging Resistance (hours) |
|---|---|---|---|---|
| | | 4 | None | 0.5 or less |
| | | 5 | 2,6-di-tert-butyl-4-methylphenol | 1 or less |
| | | 6 | 2,2'-methylenebis(6-tert-butyl-4-methylphenol) | 17 |
| | | 7 | 4,4'-butylidenbis(2-tert-butyl-5-methylphenol) | 16 |
| | | 8 | 1,1,3-tris(5-tert-butyl-4-hydroxy-2-methylphenyl)-butane | 36 |
| 21 | 58 | | Tetrakis[3-[3-(3,5-di-tert-butyl-2-hydroxyphenyl)-propylthio]propionyloxymethyl]methane | 200 |
| 22 | 70 | | Bis[2,2,2-tris[3-[3-(3,5-di-tert-butyl-2-hydroxyphenyl)propylthio]propionyloxymethyl]ethyl]ether | 200 |
| 23 | 73 | | 1,3,5-tris[2-[3-[3-(tert-butyl-2-hydroxy-5-methylphenyl)propylthio]propionyloxy]ethyl]-1,3,5-triazine-2,4,6(1H, 3H, 5H)-trione | 190 |

While the invention has been described in detail and with reference to specific embodiments thereof, it will be apparent to one skilled in the art that various changes and modifications can be made therein without departing from the spirit and scope thereof.

What is claimed is:

1. A phenol derivative of the formula

TABLE 7

| Application Example | Illustrative Compound No. | Comparative Example | Antioxidant | $MFR_1$ | $MFR_4$ |
|---|---|---|---|---|---|
| | | 1 | None | 12.3 | 50 or more |
| | | 2 | 4,4'-butylidenebis(2-tert-butyl-5-methylphenol) | 7.2 | 13.5 |
| | | 3 | Tetrakis[3-(3,5-di-tert-butyl-4-hydroxylphenyl)propionyloxymethyl]methane | 6.5 | 12.2 |
| 17 | 57 | | Tetrakis[3-[3-(3-tert-butyl-2-hydroxy-5-methylphenyl)propylthio]propionyloxymethyl]methane | 4.4 | 5.6 |
| 18 | 62 | | 1,1,1-tris[3-[3-(3,5-di-tert-butyl-2-hydroxyphenyl)-propylthio]propionyloxymethyl]propane | 4.5 | 6.2 |
| 19 | 69 | | Bis[2,2,2-tris[3-[3-(3-tert-butyl-2-hydroxy-5-methylphenyl)propylthio]propionyloxymethyl]ethyl]ether | 4.1 | 5.3 |
| 20 | 73 | | 1,3,5-tris[2-[3-[3-tert-butyl-2-hydroxy-5-methylphenyl)propylthio]propionyloxy]ethyl]-1,3,5-triazine-2,4,6(1H, 3H, 5H)-trione | 4.6 | 7.1 |

APPLICATION EXAMPLES 21 TO 23

0.10 wt% of the antioxidant as shown in Table 8 was added to powder of propylene-ethylene block copolymer having an intrinsic viscosity of 2.3 (as measured in tetralin at 135° C.) and containing 13 wt% of ethylene, followed by thorough mixing using a mixer. The pow-

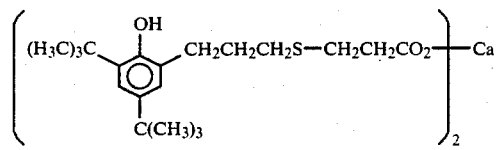

* * * * *